US009795674B2

(12) United States Patent
Parshad et al.

(10) Patent No.: US 9,795,674 B2
(45) Date of Patent: Oct. 24, 2017

(54) STABLE ANTIBODY CONTAINING COMPOSITIONS

(75) Inventors: Henrik Parshad, Viby Sj. (DK); Dorthe Kot Engelund, Holte (DK); Malin Therese Gustavsson, Frederiksberg C. (DK)

(73) Assignee: Novo Nordisk A/S, Bagsvaerd (DK)

( * ) Notice: Subject to any disclaimer, the term of this patent is extended or adjusted under 35 U.S.C. 154(b) by 376 days.

(21) Appl. No.: 13/580,041

(22) PCT Filed: Feb. 28, 2011

(86) PCT No.: PCT/EP2011/052914
§ 371 (c)(1),
(2), (4) Date: Oct. 5, 2012

(87) PCT Pub. No.: WO2011/104381
PCT Pub. Date: Sep. 1, 2011

(65) Prior Publication Data
US 2013/0028907 A1    Jan. 31, 2013

Related U.S. Application Data

(60) Provisional application No. 61/310,480, filed on Mar. 4, 2010.

(30) Foreign Application Priority Data

Feb. 26, 2010 (EP) .................... 10154771

(51) Int. Cl.
A61K 39/395 (2006.01)
(52) U.S. Cl.
CPC ............... A61K 39/39591 (2013.01)
(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,789,192 A | 8/1998 | Moore et al. |
| 5,843,725 A | 12/1998 | Sledziewski et al. |
| 5,945,511 A | 8/1999 | Lok et al. |
| 5,985,614 A | 11/1999 | Rosen et al. |
| 6,020,163 A | 2/2000 | Conklin |
| 6,165,467 A | 12/2000 | Hagiwara et al. |
| 6,486,301 B1 | 11/2002 | Ebner et al. |
| 6,610,286 B2 | 8/2003 | Thompson et al. |
| 6,685,940 B2 | 2/2004 | Andya et al. |
| 6,733,792 B1 | 5/2004 | Lu |
| 6,875,432 B2 | 4/2005 | Liu et al. |
| 7,074,912 B2 | 7/2006 | Eaton et al. |
| 7,101,539 B2 | 9/2006 | Heuer et al. |
| 7,122,352 B2 | 10/2006 | Conklin et al. |
| 7,189,394 B2 | 3/2007 | Thompson et al. |
| 7,271,246 B2 | 9/2007 | Conklin et al. |
| 7,364,732 B2 | 4/2008 | Thompson et al. |
| 7,393,694 B1 | 7/2008 | Schlein et al. |
| 7,537,761 B2 | 5/2009 | Xu et al. |
| 7,582,287 B2 | 9/2009 | Chandrasekher et al. |
| 7,601,830 B2 | 10/2009 | Conklin et al. |
| 8,102,478 B2 | 1/2012 | Xue |
| 8,361,469 B2 * | 1/2013 | Hilden .................. C07K 16/38 424/133.1 |
| 8,603,470 B1 | 12/2013 | Chang |
| 2002/0042366 A1 | 4/2002 | Thompson et al. |
| 2002/0045571 A1 | 4/2002 | Liu et al. |
| 2002/0099179 A1 | 7/2002 | Jolliffe et al. |
| 2003/0073638 A1 * | 4/2003 | Kjalke .................. A61K 38/45 514/14.3 |
| 2003/0108549 A1 | 6/2003 | Carter et al. |
| 2003/0157096 A1 | 8/2003 | Kindsvogel et al. |
| 2003/0180287 A1 | 9/2003 | Gombotz et al. |
| 2004/0005320 A1 | 1/2004 | Thompson et al. |
| 2004/0009168 A1 | 1/2004 | Kaisheva et al. |
| 2004/0018200 A1 | 1/2004 | Oliver et al. |
| 2004/0022792 A1 | 2/2004 | Klinke et al. |
| 2004/0152878 A1 | 8/2004 | Conklin et al. |
| 2004/0181040 A1 | 9/2004 | Conklin et al. |
| 2004/0191243 A1 | 9/2004 | Chen et al. |
| 2004/0197324 A1 | 10/2004 | Liu et al. |
| 2005/0053598 A1 * | 3/2005 | Burke et al. ............... 424/130.1 |
| 2005/0060101 A1 | 3/2005 | Bevilacqua et al. |
| 2006/0034821 A1 | 2/2006 | Kline |
| 2006/0068471 A1 | 3/2006 | Kindsvogel et al. |

(Continued)

FOREIGN PATENT DOCUMENTS

| | | |
|---|---|---|
| EP | 1314437 A1 | 5/2003 |
| EP | 1336410 A1 | 8/2003 |

(Continued)

OTHER PUBLICATIONS

Meyer et al., Journal of Pharmaceutical Sciences, "Antimicrobial Preservative Use in Parenteral Products: Past and Present", 2007, vol. 96, No. 12, p. 3155-3167.
Siderov, Lancet Oncology, "Care With Intrathecal Trastuzumab", 2006, vol. 7, No. 11, p. 888.
Gupta et al., AAPS Pharmscitech, "Development of a Multidose Formulation for a Humanized Monoclonal Antibody Using Experimental Design Techniques", 2003, vol. 5, No. 2, pp. 1-9.
Wolfe et al., "Treatment for Rheumatoid Arthritis and the Risk of Hospitalization for Pneumonia", Arthritis & Rheumatism, Feb. 2006, vol. 54, No. 2, pp. 628-634.
Sekiguchi et al., "Messenger Ribonucleic Acid Expression Profile in Peripheral Blood Cells From RA Patients Following Treatment With an Anti-TNF-a Monoclonal Antibody, Infliximab", Rheumatology, 2008, vol. 47, pp. 780-788.
Leivo-Korpela et al., "Adipokine Resistin Predicts Anti-Inflammatory Effect of Glucocorticoids in Asthma", Journal of Inflammation, 2011, vol. 8, No. 12, p. 1-7.
Sarchielli et al., "Fibroblast Growth Factor-2 Levels Are Elevated in the Cerebrospinal Fluid of Multiple Sclerosis Patients", Neuroscience Letters, 2008, vol. 435, p. 223-228.

(Continued)

Primary Examiner — Yunsoo Kim
(74) Attorney, Agent, or Firm — Jianjie Hu

(57) ABSTRACT

The invention relates to stable and low viscous (<50 cP) protein containing compositions, in particular, but not exclusively stable antibody containing compositions and to the use of said stable proteins in therapy, in particular for the subcutaneous delivery of said stable protein.

16 Claims, 3 Drawing Sheets

(56) References Cited

U.S. PATENT DOCUMENTS

| | | |
|---|---|---|
| 2006/0177447 A1 | 8/2006 | Xu |
| 2006/0287507 A1 | 12/2006 | Conklin et al. |
| 2007/0020255 A1 | 1/2007 | Ueno et al. |
| 2007/0053871 A1 | 3/2007 | Li et al. |
| 2007/0116700 A1 | 5/2007 | Liu et al. |
| 2007/0141670 A1 | 6/2007 | Conklin et al. |
| 2007/0184050 A1 | 8/2007 | Ishikawa et al. |
| 2008/0071063 A1 | 3/2008 | Allan et al. |
| 2008/0112953 A1 | 5/2008 | McAuley et al. |
| 2008/0171041 A1 | 7/2008 | Thompson et al. |
| 2009/0060906 A1 | 3/2009 | Barry et al. |
| 2009/0169581 A1 | 7/2009 | Sandrine |
| 2009/0226426 A1 | 9/2009 | Thompson et al. |
| 2009/0280129 A1 | 11/2009 | Liu et al. |
| 2009/0312236 A1 | 12/2009 | Beals et al. |
| 2010/0015703 A1 | 1/2010 | Conklin et al. |
| 2011/0091457 A1 | 4/2011 | Verweij et al. |
| 2013/0136733 A1 | 5/2013 | Parshad et al. |

FOREIGN PATENT DOCUMENTS

| | | | |
|---|---|---|---|
| EP | 1475100 A1 | 11/2004 | |
| EP | 1475101 A1 | 11/2004 | |
| EP | 1977763 A1 | 10/2008 | |
| EP | 1981824 A2 | 10/2008 | |
| EP | 2196476 A1 | 6/2010 | |
| JP | WO97/23509 | * | 7/1997 |
| JP | 2001-500369 A | 1/2001 | |
| JP | 2003-514027 A | 4/2003 | |
| JP | 2003-533469 A | 11/2003 | |
| JP | 2007-537703 A | 12/2007 | |
| JP | 2001-547141 | 2/2008 | |
| KR | 10-2009-0106575 | 10/2009 | |
| WO | 92/07584 | 5/1992 | |
| WO | 98/00870 A1 | 1/1998 | |
| WO | 98/48837 | 11/1998 | |
| WO | 99/03982 A1 | 1/1999 | |
| WO | 99/37772 A1 | 7/1999 | |
| WO | 99/46281 A2 | 9/1999 | |
| WO | 99/46379 | 9/1999 | |
| WO | 99/61630 A2 | 12/1999 | |
| WO | 99/62934 | 12/1999 | |
| WO | 0015224 A1 | 3/2000 | |
| WO | 00/39161 A1 | 7/2000 | |
| WO | 00/73454 | 12/2000 | |
| WO | 01/24814 A1 | 4/2001 | |
| WO | 01/46232 A2 | 6/2001 | |
| WO | 02/11753 A1 | 2/2002 | |
| WO | 02/13860 A1 | 2/2002 | |
| WO | 02/30463 A2 | 4/2002 | |
| WO | 02/072607 | 9/2002 | |
| WO | 03/009817 A2 | 2/2003 | |
| WO | 03/028630 A2 | 4/2003 | |
| WO | 03/068259 A1 | 8/2003 | |
| WO | 03/068260 A1 | 8/2003 | |
| WO | 03/082212 A2 | 10/2003 | |
| WO | 03/103589 A2 | 12/2003 | |
| WO | 04/001007 A2 | 12/2003 | |
| WO | 2004/009479 A1 | 1/2004 | |
| WO | 2004/016243 A2 | 2/2004 | |
| WO | 2004/016286 A2 | 2/2004 | |
| WO | 2004/039826 A1 | 5/2004 | |
| WO | 2004055164 A2 | 7/2004 | |
| WO | 2005/123131 A2 | 12/2005 | |
| WO | 2007/003936 A1 | 1/2007 | |
| WO | 2007/006858 A2 | 1/2007 | |
| WO | 2007/037795 A2 | 4/2007 | |
| WO | 2007/038501 A2 | 4/2007 | |
| WO | 2007038754 A2 | 4/2007 | |
| WO | 2007/092772 A2 | 8/2007 | |
| WO | 2007/105133 A2 | 9/2007 | |
| WO | 2007/108559 A1 | 9/2007 | |
| WO | 2007100643 A2 | 9/2007 | |
| WO | 2007/135568 A2 | 11/2007 | |
| WO | 2007/147001 A2 | 12/2007 | |
| WO | 2007149814 A1 | 12/2007 | |
| WO | 2008/009545 | 1/2008 | |
| WO | 2008/045563 | 4/2008 | |
| WO | 2008/048986 A2 | 4/2008 | |
| WO | 2008/056198 A1 | 5/2008 | |
| WO | 2008/071394 A1 | 6/2008 | |
| WO | 2008/086395 A2 | 7/2008 | |
| WO | 2008/104608 A1 | 9/2008 | |
| WO | 2008/121615 A2 | 10/2008 | |
| WO | 2008/132176 A2 | 11/2008 | |
| WO | 2008/132439 A2 | 11/2008 | |
| WO | 2008/154423 A2 | 12/2008 | |
| WO | 2008/157282 A1 | 12/2008 | |
| WO | 2008/157356 A2 | 12/2008 | |
| WO | 2008157409 A1 | 12/2008 | |
| WO | 2009/009406 A1 | 1/2009 | |
| WO | 2009/009407 A1 | 1/2009 | |
| WO | 2009013538 A2 | 1/2009 | |
| WO | 2009015398 A1 | 1/2009 | |
| WO | 2009/070642 A1 | 6/2009 | |
| WO | 2009/077483 | 6/2009 | |
| WO | 2009/103113 A1 | 8/2009 | |
| WO | 2009/120684 A1 | 10/2009 | |
| WO | 2010/000721 | 1/2010 | |
| WO | 2010/031720 A2 | 3/2010 | |
| WO | 10025369 A2 | 3/2010 | |
| WO | 2010/072691 | 7/2010 | |
| WO | 2010/113096 A1 | 10/2010 | |
| WO | 2011/028945 A1 | 3/2011 | |
| WO | 2011047073 A2 | 4/2011 | |
| WO | 2011/147921 A1 | 12/2011 | |
| WO | 2011/154139 A2 | 12/2011 | |

OTHER PUBLICATIONS

Rioja et al., "Potential Novel Biomarkers of Disease Activity in Rheumatoid Arthritis Patients", Arthritis & Rheumatism, August 2008, vol. 58, No. 8, pp. 2257-2267.

Pyrpasopoulou et al., "Response to Rituximab and Timeframe to Relapse in Rheumatoid Arthritis Patients—Association With B-Cell Markers", Mol. Diagn. Ther., 2010, vol. 14, No. 1, pp. 43-48.

Shi et al. "A Novel Cytokine Receptor-Ligand Pair" 2000. J Bio Chem vol. 275: 19167-19176.

Tsuji, H et al. Japanese Journal of Clinical and Experimental Medicine 1995 vol. 174(14): 1040-1044.

Benedetti et al. 1999, "Interleukin 8 and monocyte chemoattractant protein-1 in patients with juvenile rheumatoid arthritis. Relation to onset types, disease activity, and synovial fluid leukocytes." J. Rheumatol. vol. 26: 425-231.

Takahashi et al 1999, "The participation of IL-8 in the synovial lesions at an early stage of rheumatoid arthritis" J. Exp. Med. vol. 188: 75-87.

Gudmundsson and Hunninghake, "Respiratory Epithelial Cells Release Interleukin-8 in Response to a Thermophilic Bacteria That Causes Hypersensitivity Pneumonitis." 1999, Exp. Lung Res. vol. 25: 217-228.

Mukaida et al, 1998, "Inhibition of Neutrophil-mediated acute inflammatory injusy by an antibody against interlukin-8 (IL-8)." Inflamm. Res. Suppl. 3: S151-S157.

Yousefi et al. 1995, "Interleukin-8 is expressed by human peripheral blood eosinophils: Evidence for increased secretion in asthma" J Immunol. vol. 154: 5481-5490.

Borreback, Carl AK et al Human therapeutic antibodies Current Opinion in Pharmacology vol. 1: 404-408 (2001).

Choy, Ernest. Clinical trial outcome of anti-tumor necrosis factor alpha therapy in rhematic arthritis Cytokine, vol. 28: 158-161 (2004).

Davis, Samuel et al Isolation of Angiopoietin-1, a Ligand for the TIE2 Receptor by Secretion-Trap Expression Cloning, Cell, vol. 87: 1161-1169 (1996).

Dynan, William S et al. Control of eukaryotic messenger RNA synthesis by sequence-specific DNA binding proteins Nature vol. 316(6031): 774-778 (1985).

Incyte Pharmaceuticals, Inc, INC819592, 1 page, dated Mar. 5, 1996.

(56) References Cited

OTHER PUBLICATIONS

Eliane et al "Transforming Growth Factor Alpha: Mutation of Aspartic Acid 47 and Leucine 48 Results in Different Biological Activities" Molecular and Cellular Biology. vol. 8(3): 1247-1252 (1988).
Lederman, Seth et al. A Single Amino Acid Substitution in a Common African Allele of the CD4 Molecule Ablates Binding of the Monoclonal Antibody OKT4 Molecular Immunology vol. 28(11):1171-1181 (1991).
Li, Choh Hao et al. Beta-Endorphin omission analogs: Dissociation of immunoreactivity from other biological activities, Proc Natl Acad Sci USA, vol. 77(6): 3211-3214 (1980).
McKinnon, Murray et al. Strategies for the Discovery of Cytokine Receptor Antagonist, Drug News and Perspectives, vol. 9: 389-398 (1996).
Mijares, Alfredo et al. From Agonists to Antagonists: Fab Fragments of the Agonist-like Monoclonal Anti-beta2- Adrenoceptor Antibody Behave as Antagonist, Molecular Pharmacology, vol. 58: 373-379 (2000).
Mohler, KM et al Immunotherapeutic Potential of Soluble Cytokine Receptors in Inflammatory Disease, FASEB J, US Fed of American Soc for Experimental Biology, vol. 6(4): A1123, Poster Presentation No. 1086 (1992).
Rich, Benjamin et al. Cytokines: IL-20—a new effector in skin inflammation, Current Biology vol. 11:R531-R534 (2001).
Robinson, Clifford R et al. Optimizing the stability of single-chain proteins by linker length and composition mutagenesis, Proc Natl Acad Sci USA vol. 95: 5929-5934 (1998).
Rose-John, Stefan Interleukin-6 biology is coordinated by membrane bound and soluble receptors, Acta Biochimica Polonica. vol. 50(3): 603-611 (2003).
Stenderup, Karin et al interleukin-20 as a target in psoriasis treatment. Ann NY Acad Sci vol. 1110: 368-381 (2007).
Volk, Hans-Dieter et al, IL-10 and its homologs: important immune mediators and emerging immunotherapeutic agents Trends in Immunology, vol. 22(8): 414-417 (2001).
Wells, James A. Additivity of Mutational Effects in Proteins Biochemistry, vol. 29(37): 8509-8517 (1990).
Wolfe, Frederick et al. Treatment for Rheumatoid Arthritis and the risk of Hospitalization for Pneumonia Arthritis and Rheumatism vol. 54(2): 628-634 (2006).
Lequerre Thierry et al, "Gene profiling in white blood cells predicts infliximab responsiveness in rheumatoid arthritis" Arthritis Research and Therapy, vol. 8(4): R105 (2006).
Sekiguchi, N. et al. "Messenger ribonucleic acid expression profile in peripheral blood cells from RA patients following treatment with an anti-TNF-alpha monoclonal antibody, infliximab" Rheumatology vol. 47(6): 780-788 (2006).
Tanino M et al. "Prediction of efficacy of anti-TNF biologic agent, infliximab, for rheumatoid arthritis patients using a comprehensive transcriptome analysis of white blood cells." Biochemical and Biophysical Research Communications vol. 387(2): 261-265 (2009).
Julia Antonio et al. "Identification of candidate genes for rituximab response in rheumatoid arthritis patients by microarray expression profiling in blood cells." Pharmacogenomics, vol. 10(10): 1697-1708 (2009).
Sirpa Leivo-Korpela et al "Adipokine resistin predicts anti-inflammatory effect of glucocorticoids in asthma" Journal of Inflammation, vol. 8(1): 12 (2011).
Sarchuelli, P et al. "Fibroblast growth factor02 levels are elevated in the cerebrospinal fluid of multiple sclerosis patients." Neuroscience Letters. vol. 435(3): 223-228 (2008).
Nakada S et al. "Identification of candidate genes involved in endogenous protection mechanisms against acute pancreatitis in mice." Biochemical and Biophysical Research Communications vol. 391(3): 1342-1347 (2010).
Pyrpasopoulou et al. Mol. Diagn. Ther. vol. 14(1): 43-48 (2010).
Rioja et al, "Potential Novel Biomarkers of Disease Activity in Rheumatoid Arthritis Patients" Arthritis and Rheum. vol. 58(8): 2257-2267 (2008).
Otkjaer, K et al. "IL-20 Gene Expression is Induced by IL-1beta through Mitogen-Activated Protein Kinase and NF-kappaB-Dependent Mechanisms." J Invest Dermatol. 2007 vol. 127(6):1326-1336.
Blumberg, H. et al. "Interleukin 20: discovery, receptor identification, and role in epidermal function." Cell, vol. 104:9-19, 2001.
Wei, et al. "IL-20: biological functions and clinical implications" J. Biomed. Sci. vol. 13(5): 601-612. 2006.
Shi et al., "A Novel Cytokine Receptor-Ligand Pair", Journal of Biological Chemistry, Jun. 23, 2000, vol. 275, No. 25, pp. 19167-19176.
Borrebaeck et al., "Human Therapeutic Antibodies", Current Opinion in Pharmacology, 2001, vol. 1, pp. 404-408.
Choy, "Clinical Trial Outcome of Anti-Tumour Necrosis Factor Alpha Therapy in Rheumatic Arthritis", Cytokine, 2004, vol. 28, pp. 158-161.
Davis et al., "Isolation of Angiopoietin-1, A Ligand for the TIE2 Receptor, by Secretion-Trap Expression Cloning", Cell, 1996, vol. 87, pp. 1161-1169.
Dynan et al., "Control of Eukaryotic Messenger RNA Synthesis by Sequence-Specific DNA-Binding Proteins", Nature, Aug. 1985, vol. 316, No. 29, p. 774-778.
Lederman et al., "A Single Amino Acid Substitution in a Common African Allele of the CD4 Molecule Ablates Binding of the Monoclonal Antibody, OKT4", Molecular Immunology, 1991, vol. 28, No. 11, pp. 1171-1181.
Li et al., "β-Endorphin Omission Analogs: Dissociation of Immunoreactivity From Other Biological Activities", Proc. Natl. Acad. Sci. USA, Jun. 1980, vol. 77, No. 6, p. 3211-3214.
Mijares et al., "From Agonist to Antagonist: FAB Fragments of an Agonist-Like Monoclonal Anti-β-Adrenoceptor Antibody Behave As Antagonists", Molecular Pharmacology, 2000, vol. 58, pp. 373-379.
Rich et al., "Cytokines: IL-20—A New Effector in Skin Inflammation", Current Biology, 2001, vol. 11, pp. R531-R534.
Robinson et al., "Optimizing the Stability of Single-Chain Proteins by Linker Length and Composition Mutagenesis", Proc. Natl. Acad. Sci. USA, May 1998, vol. 95, pp. 5929-5934.
Stenderup et al., "Interleukin-20 As a Target in Psoriasis Treatment", Ann. N.Y. Acad. Sci. 2007, vol. 1110, pp. 368-381.
Volk et al., "IL-20 and Its Homologs: Important Immune Mediators and Emerging Immunotherapeutic Agents", Trends in Immunology, 2001, vol. 22, No. 8, pp. 414-417.
Wells, "Additivity of Mutational Effects in Proteins", Biochemistry, Sep. 1990, vol. 29, No. 37, pp. 8509-8517.
Seyrek N et al.,Is there any relationship between serum levels of interleukin-10 and atherosclerosis in hemodialysis patients. Journal :Scandinavian Journal of Urology and Nephrology, Year 2005, vol. 39, pp. 405-409.
Pasqui A.L.,Pro-inflammatory/anti-inflammatory cytokine imbalance in acute coronary syndromes,Journal :Clinical and Experimental Medicine, Year 2006, vol. 6, pp. 38-44.
Hsu Yu-Hsiang,Anti-IL-20 monoclonal antibody inhibits the differentiation of osteoclasts and protects against osteoporotic bone loss, Journal: Journal of Experimental Medicine, Year 2011,vol. 208 No. 9 pp. 1849-1861.
Bei Chen et al . Influence of histidine on the stability and physical properties of a fully antibody in aqueous and solid forms. Journal:Pharmaceutical research Year 2003 vol. 20. Issue 12 pp. 1952-1960.
Salinas et al., "Understanding and Modulating Opalescence and Viscosity in a Monoclonal Antibody Formulation", Journal of Pharmaceutical Sciences, 2010, vol. 99, No. 1, p. 82-93.
Clackson et al., "Making Antibody Fragments Using Phage Display Libraries", Nature, 1991, vol. 352, pp. 624-628.
Marks et al., "By-Passing Immunization: Human Antibodies From V-Gene Libraries Displayed on Phage", Journal of Molecular Biology, 1991, vol. 22, pp. 581-597.

(56) References Cited

OTHER PUBLICATIONS

Morrison et al., "Chimeric Human Antibody Molecules: Mouse Antigen-Binding Domains With Human Constant Region Domains", Proceedings of the National Academy of Sciences USA, 1984, vol. 81, pp. 6851-6855.
Luo et al., "High-Concentration UF/DF of a Monoclonal Antibody", Bioprocess International, 2006, vol. 4, No. 2, pp. 44-48.
Kohler et al:, "Continuous Cultures of Fused Cells Secreting Antibody of Predefined Specificity", Nature, 1975, vol. 256, pp. 495-497.
Product catalog file from R&D Systems as of Aug. 14, 2007 for anti-IL-20 antibody.
mAb1102 from R&D Systems reference sheet Rev. Jun. 17, 2011.
Excerpt from the International Immunogenetics Information System (IMGT) Retrieved on Oct. 28, 2014.
Excerpt from the website "Clinical Trials.gov". retrieved on Oct. 28, 2014.
Excerpt from the website Advances in Drug Discovery. Retrieved on Oct. 28, 2014.
Panka D J et al: "Variable Region Framework Differences Result in Decreased or Increased Affinity of Variant Anti-Digoxin Antibodies",Journal :Proceedings of the National Academy of Sciences,National Academy of Sciences, US,Year:May 1, 1988 vol. 85, No. 9, pp. 3080-3084.
Ann L. Daugherty et al., "Formulation and delivery issues for monoclonal antibody therapeutics", Advanced Drug Delivery Reviews, 2006, vol. 58, pp. 686-706.

\* cited by examiner

SEQUENCE LISTING

<160> NUMBER OF SEQ ID NOS: 12

<210> SEQ ID NO 1
<211> LENGTH: 339
<212> TYPE: DNA
<213> ORGANISM: Artificial Sequence
<220> FEATURE:
<223> OTHER INFORMATION: Humanized variable light chain

<400> SEQUENCE: 1

```
gacatcgtga tgacccagac ccctctgtcc ctgtccgtga cccctggcca gcctgcctcc    60
atctcctgca gtcctccca gtccctgctg gaatccgacg gcaagaccta cctgaactgg   120
tatctgcaga gcctggcca gtcccctcag ctgctgatct acctggtgtc catcctggac   180
tccggcgtgc ctgaccggtt ctccggctcc ggcagcggca ccgacttcac cctgaagatc   240
tcccgggtgg aggccgagga cgtgggcgtg tactactgcc tgcaggccac ccacttccct   300
cagacctttg gcggcggaac aaaggtggag atcaagcgt                         339
```

<210> SEQ ID NO 2
<211> LENGTH: 339
<212> TYPE: DNA
<213> ORGANISM: Artificial Sequence
<220> FEATURE:
<223> OTHER INFORMATION: Humanized variable light chain

<400> SEQUENCE: 2

```
ctgtagcact actgggtctg gggagacagg gacaggcact ggggaccggt cggacggagg    60
tagaggacgt tcaggagggt cagggacgac cttaggctgc cgttctggat ggacttgacc   120
atagacgtct tcggaccggt caggggagtc gacgactaga tggaccacag gtaggacctg   180
aggccgcacg gactggccaa gaggccgagg ccgtcgccgt ggctgaagtg ggacttctag   240
agggcccacc tccggctcct gcacccgcac atgatgacgg acgtccggtg ggtgaaggga   300
gtctggaaac cgccgccttg tttccacctc tagttcgca                         339
```

<210> SEQ ID NO 3
<211> LENGTH: 113
<212> TYPE: PRT
<213> ORGANISM: Artificial Sequence
<220> FEATURE:
<223> OTHER INFORMATION: Humanized variable light chain

<400> SEQUENCE: 3

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg
```

<210> SEQ ID NO 4
<211> LENGTH: 363
<212> TYPE: DNA
<213> ORGANISM: Artificial Sequence
<220> FEATURE:
<223> OTHER INFORMATION: Humanized variable heavy chain

<400> SEQUENCE: 4

```
gaggtgcagc tggtcgagtc tggcggcgga ctggtgaagc ctggcggctc cctgcggctg      60
tcctgcgctg cctccggctt caccttctcc aactacgcca tgtcctgggt gcggcagacc     120
ccagaaaagc ggctgaatgg gtggccacc atctcccggt ccggctccta ctcctacttc      180
cctgactccg tgcagggccg gttcaccatc agcagggaca cgccaagaa ctccctgtac      240
ctgcagatga actccctgag agccgaggac acagccgtgt actactgcgc caggctgggc     300
ggctacgacg agggcgacgc catggacagc tggggccagg gcaccaccgt gaccgtgtcc     360
tcc                                                                   363
```

<210> SEQ ID NO 5
<211> LENGTH: 363
<212> TYPE: DNA
<213> ORGANISM: Artificial Sequence
<220> FEATURE:
<223> OTHER INFORMATION: Humanized variable heavy chain

<400> SEQUENCE: 5

```
ctccacgtcg accagctcag accgccgcct gaccacttcg gaccgccgag ggacgccgac      60
aggacgcgac ggaggccgaa gtggaagagg ttgatgcggt acaggaccca cgccgtctgg    120
ggtcttttcg ccgaccttac ccaccggtgg tagagggcca ggccgaggat gaggatgaag    180
ggactgaggc acgtcccggc caagtggtag tcgtccctgt tgcggttctt gagggacatg    240
gacgtctact tgagggactc tcggctcctg tgtcggcaca tgatgacgcg gtccgacccg    300
ccgatgctgc tcccgctgcg gtacctgtcg accccggtcc cgtggtggca ctggcacagg    360
agg                                                                   363
```

<210> SEQ ID NO 6
<211> LENGTH: 121
<212> TYPE: PRT
<213> ORGANISM: Artificial Sequence
<220> FEATURE:
<223> OTHER INFORMATION: Humanized variable heavy chain

<400> SEQUENCE: 6

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110
```

Gln Gly Thr Thr Val Thr Val Ser Ser
        115                 120

<210> SEQ ID NO 7
<211> LENGTH: 657
<212> TYPE: DNA
<213> ORGANISM: Artificial Sequence
<220> FEATURE:
<223> OTHER INFORMATION: Humanized constant light chain

<400> SEQUENCE: 7
gacatcgtga tgacccagac ccctctgtcc ctgtccgtga cccctggcca gcctgcctcc     60
atctcctgca gtcctccca gtccctgctg aatccgacg gcaagaccta cctgaactgg     120
tatctgcaga gcctggcca gtcccctcag ctgctgatct acctggtgtc catcctggac     180
tccggcgtgc ctgaccggtt ctccggctcc ggcagcggca ccgacttcac cctgaagatc     240
tcccgggtgg aggccgagga cgtgggcgtg tactactgcc tgcaggccac ccacttccct     300
cagacctttg gcggcggaac aaaggtggag atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt     657

<210> SEQ ID NO 8
<211> LENGTH: 657
<212> TYPE: DNA
<213> ORGANISM: Artificial Sequence
<220> FEATURE:
<223> OTHER INFORMATION: Humanized constant light chain

<400> SEQUENCE: 8
ctgtagcact actgggtctg gggagacagg gacaggcact ggggaccggt cggacggagg     60
tagaggacgt tcaggagggt cagggacgac cttaggctgc cgttctggat ggacttgacc     120
atagacgtct tcgaccggt caggggagtc gacgactaga tggaccacag gtaggacctg     180
aggccgcacg gactggccaa gaggccgagg ccgtcgccgt ggctgaagtg ggacttctag     240
agggcccacc tccggctcct gcaccggcac atgatgacgg acgtccggtg ggtgaaggga     300
gtctggaaac cgccgccttg tttccacctc tagttcgcat gccaccgacg tggtagacag     360
aagtagaagg gcggtagact actcgtcaac tttagacctt gacggagaca acacacggac     420
gacttattga agatagggtc tctccggttt catgtcacct tccacctatt gcgggaggtt     480
agcccattga gggtcctctc acagtgtctc gtcctgtcgt tcctgtcgtg gatgtcggag     540
tcgtcgtggg actgcgactc gtttcgtctg atgctctttg tgtttcagat gcggacgctt     600
cagtgggtag tcccggactc gagcgggcag tgtttctcga gttgtccccc tctcaca       657

<210> SEQ ID NO 9
<211> LENGTH: 219
<212> TYPE: PRT
<213> ORGANISM: Artificial Sequence
<220> FEATURE:
<223> OTHER INFORMATION: Humanized constant light chain

<400> SEQUENCE: 9

Asp Ile Val Met Thr Gln Thr Pro Leu Ser Leu Ser Val Thr Pro Gly
1               5                   10                  15

```
Gln Pro Ala Ser Ile Ser Cys Lys Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 1344
<212> TYPE: DNA
<213> ORGANISM: Artificial Sequence
<220> FEATURE:
<223> OTHER INFORMATION: Humanized constant heavy chain

<400> SEQUENCE: 10
gaggtgcagc tggtcgagtc tggcggcgga ctggtgaagc ctggcggctc cctgcggctg    60
tcctgcgctg cctccggctt caccttctcc aactacgcca tgtcctgggt gcggcagacc   120
ccagaaaagc ggctggaatg ggtggccacc atctcccggt ccggctccta ctcctacttc   180
cctgactccg tgcagggccg gttcaccatc agcagggaca cgccaagaa ctccctgtac   240 ctgcagatga actccctgag agccgaggac acagccgtgt actactgcgc caggctgggc   300
ggctacgacg agggcgacgc catggacagc tggggccagg gcaccaccgt gaccgtgtcc   360
tccgctagca ccaagggccc atccgtcttc cccctggcgc cctgctccag gagcacctcc   420
gagagcacag ccgccctggg ctgcctggtc aaggactact ccccgaacc ggtgacggtg   480 tcgtggaact caggcgccct gaccagcggc gtgcacacct tcccggctgt cctacagtcc   540
tcaggactct actccctcag cagcgtggtg accgtgccct ccagcagctt gggcacgaag   600
acctacacct gcaacgtaga tcacaagccc agcaacacca aggtggacaa gagagttgag   660
tccaaatatg gtcccccatg cccaccatgc ccagcacctg agttcctggg ggaccatca   720 gtcttcctgt tccccccaaa acccaaggac actctcatga tctcccggac ccctgaggtc   780
acgtgcgtgt ggtggacgt gagccaggaa gaccccgagg tccagttcaa ctggtacgtg   840
gatggcgtgg aggtgcataa tgccaagaca aagccgcggg aggagcagtt caacagcacg   900
```

| | |
|---|---|
| taccgtgtgg tcagcgtcct caccgtcctg caccaggact ggctgaacgg caaggagtac | 960 |
| aagtgcaagg tctccaacaa aggcctcccg tcctccatcg agaaaaccat ctccaaagcc | 1020 |
| aaagggcagc cccgagagcc acaggtgtac accctgcccc catcccagga ggagatgacc | 1080 |
| aagaaccagg tcagcctgac ctgcctggtc aaaggcttct accccagcga catcgccgtg | 1140 |
| gagtgggaga gcaatgggca gccggagaac aactacaaga ccacgcctcc cgtgctggac | 1200 |
| tccgacggct ccttcttcct ctacagcagg ctaaccgtgg acaagagcag gtggcaggag | 1260 |
| gggaatgtct tctcatgctc cgtgatgcat gaggctctgc acaaccacta cacacagaag | 1320 |
| agcctctccc tgtctctggg taaa | 1344 |

<210> SEQ ID NO 11
<211> LENGTH: 1344
<212> TYPE: DNA
<213> ORGANISM: Artificial Sequence
<220> FEATURE:
<223> OTHER INFORMATION: Humanized constant heavy chain

<400> SEQUENCE: 11

| | |
|---|---|
| ctccacgtcg accagctcag accgccgcct gaccacttcg gaccgccgag ggacgccgac | 60 |
| aggacgcgac ggaggccgaa gtggaagagg ttgatgcggt acaggaccca cgccgtctgg | 120 |
| ggtcttttcg ccgaccttac ccaccggtgg tagaggggcca ggccgaggat gaggatgaag | 180 |
| ggactgaggc acgtcccggc caagtggtag tcgtccctgt tgcggttctt gagggacatg | 240 |
| gacgtctact tgagggactc tcggctcctg tgtcggcaca tgatgacgcg gtccgacccg | 300 |
| ccgatgctgc tcccgctgcg gtacctgtcg accccggtcc cgtggtggca ctggcacagg | 360 |
| aggcgatcgt ggttcccggg taggcagaag ggggaccgcg ggacgaggtc ctcgtggagg | 420 |
| ctctcgtgtc ggcgggaccc gacggaccag ttcctgatga aggggcttgg ccactgccac | 480 |
| agcaccttga gtccgcggga ctggtcgccg cacgtgtgga aggccgaca ggatgtcagg | 540 |
| agtcctgaga tgagggagtc gtcgcaccac tggcacggga ggtcgtcgaa cccgtgcttc | 600 |
| tggatgtgga cgttgcatct agtgttcggg tcgttgtggt tccacctgtt ctctcaactc | 660 |
| aggtttatac cagggggtac gggtggtacg ggtcgtggac tcaaggaccc cctggtagt | 720 |
| cagaaggaca agggggttt tgggttcctg tgagagtact agagggcctg gggactccag | 780 |
| tgcacgcacc accacctgca ctcggtcctt ctggggctcc aggtcaagtt gaccatgcac | 840 |
| ctaccgcacc tccacgtatt acggttctgt ttcggcgccc tcctcgtcaa gttgtcgtgc | 900 |
| atggcacacc agtcgcagga gtggcaggac gtggtcctga ccgacttgcc gttcctcatg | 960 |
| ttcacgttcc agaggttgtt tccggagggc aggaggtagc tcttttggta gaggtttcgg | 1020 |
| tttcccgtcg gggctctcgg tgtccacatg tgggacgggg gtagggtcct cctctactgg | 1080 |
| ttcttggtcc agtcggactg gacggaccag tttccgaaga tggggtcgct gtagcggcac | 1140 |
| ctcaccctct cgttacccgt cggcctcttg ttgatgttct ggtgcggagg gcacgacctg | 1200 |
| aggctgccga ggaagaagga gatgtcgtcc gattggcacc tgttctcgtc caccgtcctc | 1260 |
| cccttacaga agagtacgag gcactacgta ctccgagacg tgttggtgat gtgtgtcttc | 1320 |
| tcggagaggg acagagaccc attt | 1344 |

<210> SEQ ID NO 12
<211> LENGTH: 448
<212> TYPE: PRT
<213> ORGANISM: Artificial Sequence
<220> FEATURE:

<223> OTHER INFORMATION: Humanized constant heavy chain

<400> SEQUENCE: 12

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Ser Gly Ser Tyr Ser Tyr Phe Pro Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Gly Tyr Asp Glu Gly Asp Ala Met Asp Ser Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Arg Leu Thr Val Asp Lys Ser
            405                 410                 415
Arg Trp Gln Glu Gly Asn Val Phe Ser Cys Ser Val Met His Glu Ala
        420                 425                 430
Leu His Asn His Tyr Thr Gln Lys Ser Leu Ser Leu Ser Leu Gly Lys
        435                 440                 445
```

STABLE ANTIBODY CONTAINING COMPOSITIONS

CROSS-REFERENCE TO RELATED APPLICATIONS

This application is a 35 U.S.C. §371 national stage application of International Patent Application PCT/EP2011/052914 (published as WO 2011/104381 A2), filed Feb. 28, 2011, which claimed priority of European Patent Application 10154771.9, filed Feb. 26, 2010; this application further claims priority under 35 U. S.C. §119 of U.S. Provisional Application 61/310,480, filed Mar. 4, 2010.

FIELD OF THE INVENTION

The invention relates to stable and low viscous liquid compositions containing proteins, in particular, but not exclusively stable antibodies, and to the use of said compositions in therapy, in particular for the subcutaneous delivery of said stable protein.

BACKGROUND OF THE INVENTION

Immunoglobulins, monoclonal antibodies (mAbs) and humanized antibodies have been in development as pharmaceutical products for a number of years. There is a clear incentive for developing high concentration liquid formulations of mAbs due to the potential of subcutaneous administration which results in higher convenience for the patient. However, there is a general consensus that development of high-concentration formulations of mAbs poses serious challenges with respect to the physical and chemical stability of the mAb such as increased formation of soluble as well as insoluble aggregates which enhance the probability of an immunogenic response as well as give rise to low bioactivity.

Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

Furthermore, high-concentration formulations of mAbs have been reported to result in increased viscosity thereby creating serious challenges for the manufacturability and injectability.

Controlling aggregation and viscosity of liquid formulations of high-concentration mAbs is not a trivial matter. The fact that only few mAb product on the market exists as a high concentration liquid formulation (≥100 mg/ml) displays the complexity. Papers have been published which show that NaCl may lower the viscosity and also to some extent control aggregation (EP 1981824). Sucrose has also shown to stabilise mAb against formation of aggregates by way of a preferential exclusion mechanism. However, identifying suitable stabilisers is still an empirical science in this field.

It is well known that relatively high amounts of electrolytes, such as salt and buffer, are used to lower the viscosity of high concentration mAb formulations (EP 1981824). WO 01/24814 (Chiron Corporation) describes liquid polypeptide-containing pharmaceutical composition comprising an amino acid base as a stabiliser. EP 1336410 (Chugai Seiyaku Kabushiki Kaisha) describes an injectable pharmaceutical formulation containing a physiologically active protein and at least one sugar as a soothing agent. EP 1314437 (Chugai Seiyaku Kabushiki Kaisha) describes an antibody containing preparation comprising a glycine and/or histidine buffer. WO 02/30463 (Genentech, Inc) describes a concentrated protein formulation having reduced viscosity and a salt and/or buffer in an amount of at least about 50 mM. EP 1475100 (Chugai Seiyaku Kabushiki Kaisha) describes an antibody containing solution comprising an organic acid and a surfactant as stabilisers. EP 1475101 (Chugai Seiyaku Kabushiki Kaisha) describes an antibody containing solution comprising a sugar as a stabiliser. WO 2004/001007 (IDEC Pharmaceuticals Corporation) describes a concentrated antibody composition consisting essentially of histidine or acetate buffer in the range of from about 2 mM to about 48 mM. WO 2004/016286 (Abbot Laboratories (Bermuda) Ltd.) describes a formulation of human antibodies having a pH of between about 4 and 8. WO 2005/123131 (Medimmune Vaccines, Inc) describes a formulation for spray drying an antibody or vaccine. WO 2007/003936 (Insense Limited) describes a stable aqueous system comprising a protein and one or more stabilising agents which have ionisable groups. WO 2007/092772 (Medimmune, Inc.) describes a liquid protein formulation comprising an Fc variant protein and between 1 mM to 100 mM buffering agent. US 2004/0022792 (Immunex Corporation) describes a method of stabilising a protein at a pH of between about 2.8 and about 4.0. US 2003/0180287 (Immunex Corporation) describes an aqueous pharmaceutical composition suitable for long term storage of polypeptides. WO 2008/071394 (F. Hoffmann-La Roche AG) describes a stable pharmaceutical parenteral formulation containing an antibody. WO 2009/120684 and WO 2008/121615 (MedImmune Inc) both describe high concentration liquid formulations of antibodies or fragments thereof that specifically bind to a human interferon alpha polypeptide. WO 2009/070642 (MedImmune Inc) describes stable lyophilized formulations of bispecific antibodies or fragments thereof. EP 1 977 763 (Chugai Seiyaku Kabushiki Kaisha) describes antibody containing stabilising compositions comprising one or more amino acids. US 2004/0197324 (Genentech, Inc) describes highly concentrated antibody and protein formulations with reduced viscosity. WO 2008/132439 (University of Strathclyde) describes precipitation stabilising compositions which are claimed to prevent or reduce aggregation. US 2007/0020255 (Kyowa Hakko Kogyo Co., Ltd) describes a method of stabilising an antibody in solution which comprises the addition of glycine and citric acid to the solution. US 2007/0184050 (Kirin Beer Kabushiki Kaisha) describes a stable liquid formulation containing an antibody in a glutamate buffer and/or a citrate buffer. US2009/0280129 (Genentech describes high concentration antibody and protein formulations.

There is therefore a great need for a stable high-concentrated pharmaceutical antibody composition having a low and feasible viscosity which is suitable for subcutaneous administration, such as in a ready to use device. Furthermore, from a patient point of view it would be highly desirable to have room temperature stable products. At this moment, there are no marketed mAb formulations where storage at room temperature is a possibility throughout the shelf life of the drug product. Typically, increased protein degradation occurs forming an un-acceptably high level of aggregates and protein related impurities, which may give rise to immunogenic reactions.

Many of the marketed mAb products contain surfactants in their formulation. Typically, surfactants are added in order to reduce interfacial stress which can induce protein aggregation and particle formation leading to unacceptable product quality. Examples of interfacial stress could be contact of the protein with i) air ii) container closure material, such as rubber plunger, piston, glass, pre-filled syringes iii) production related materials, such as steel tanks, tubings and pumps iv) ice, during freeze/thaw, etc. However, surfactants such as polysorbates typically contain a residue of peroxides which may oxidize the protein molecule leading to a compromised product quality. Furthermore, from a manufacturing point of view addition of polysorbates requires an extra step in the production since ultra/diafiltration is challenging to conduct when the formulation contains the said polysorbates. The formation of oxidized products is a challenging issue, therefore a careful handling of polysorbates is required in order to control the formation of oxidized products. Thus, it would be desirable to design formulations without surfactants, both from a stability- and manufacturing point of view.

SUMMARY OF THE INVENTION

According to a first aspect of the invention, the invention provides a stable, liquid composition comprising a protein, a salt and/or a buffer, characterised in that the total concentration of said salt and/or buffer is lower than 100 mM.

According to another aspect of the invention, there is provided a stable, liquid composition comprising protein, a salt and/or a buffer, wherein the total concentration of the salt and/or buffer is lower than 60 mM.

According to another aspect of the invention, there is provided a stable, liquid protein composition, that is stable at room temperature.

According to another aspect of the invention, there is provided a stable, liquid composition, wherein the concentration of the protein is between 100 mg/ml and 300 mg/ml.

According to another aspect of the invention, there is provided a stable, liquid protein composition where the amino acid, L-arginine is used as a stabilizer.

According to another aspect of the invention, there is provided a stable protein composition as defined herein for use in therapy.

According to another aspect of the invention, the invention provides a protein composition without adding surfactant which is both stable and feasible to produce.

DETAILED DESCRIPTION OF THE INVENTION

According to a first aspect of the invention, the invention provides a stable, liquid composition comprising a protein, a salt and/or a buffer, characterised in that the total concentration of said salt and buffer is lower than 100 mM.

Surprisingly, it has been found that stable compositions of protein with low amounts of salt and buffer has a low and feasible viscosity, such as a viscosity of <50 cP at 25° C. Low viscosity of pharmaceutical formulations is especially desirable for subcutaneous injection, but is also desirable for other liquid formulations, where it for instance improves the handling of the formulation.

The term "stable composition" refers to a composition with satisfactory physical stability, satisfactory chemical stability or satisfactory physical and chemical stability.

The term "physical stability" of the protein composition as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein compositions is evaluated by means of visual inspection and/or turbidity measurements after exposing the composition filled in suitable containers (e.g. cartridges or vials). It is an inherent quality of highly concentrated formulations of mabs to exhibit opalescence due to Raleigh scattering. Thus, a composition cannot be classified as physically unstable with respect to protein aggregation, when it shows visual turbidity in daylight. However, when there are precipitates or phase separation visible in day light the formulation is classified as physically unstable.

The term "chemical stability" of the protein composition as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein composition is well-known by the person skilled in the art. Most proteins are prone to deamidation, a process in which the side chain amide group in glutaminyl or asparaginyl residues is hydrolysed to form a free carboxylic acid. Other degradation pathways involve formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., *Plenum Press, New York* 1992). Oxidation (of for instance methionine residues) can be mentioned as another variant of chemical degradation. The chemical stability of the protein composition can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

SEC-HPLC is in particular used for quantification of protein aggregates. The samples may for instance be analysed using a TSK G3000 SWXL column, isocratic elution and subsequent UV detection at 214 nm. This method is used to determine monomeric IgG content and % HMWP consisting of dimeric species or larger which are separated according to size by the gel resin. The monomeric content and % HMWP are determined relative to the total protein content detected by the method.

Hence, as outlined above, a stable composition refers to a composition with satisfactory physical stability, satisfactory chemical stability or satisfactory physical and chemical stability. A satisfactory stability of a formulation may be one wherein less than 10% and preferably less than 5% of the protein is as an aggregate (HMWP) in the formulation. In general, a composition must be stable during use and storage (in compliance with recommended use and storage conditions) until the expiration date is reached.

Viscosity as used herein is used as the absolute viscosity also termed dynamic viscosity. Measurements are done by the cone and plate technique with a Peltier element set at 25°

C., and where a well defined shear stress gradient is applied to a sample and the resulting shear rate is measured. The viscosity is the ratio of the shear stress to the shear rate. Absolute viscosity is expressed in units of centipoise (cP) at 25° C.

The term "room temperature" as used herein, means a temperature of the room and where some kind of a cooling effect is not required. A room temperature is between 15 and 30° C., such as between 20 and 30° C., such as 20° C., 25° C. or 30° C.

The term "protein", "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g. hydroxyproline, y-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (a-aminoisobutyric acid), Abu (α-aminobutyric acid), Tle (tert-butylglycine), β-alanine, 3-aminomethyl benzoic acid and anthranilic acid.

In one embodiment, the total concentration of salt and buffer is 95 mM or lower, such as any one of 90, 85, 80, 75, 70, 65 or 60 mM or lower. In one embodiment, the total concentration of salt and buffer is lower than 60 mM, such as 50 mM or lower, such as 45, 40, 35, 33, 30, 25, 20 mM or lower.

In some embodiments, the salt can have a buffering capacity at the relevant pH, and in some embodiments, the buffer may be a salt. The critical feature is that the total concentration of salt and buffer does not exceed the stated values.

In one embodiment, the salt is an inorganic salt, or an organic salt or a combination of one or more of these. In one embodiment, the salt is selected from the group consisting of sodium chloride, magnesium chloride, sodium thiocyanate, ammonium thiocyanate, ammonium sulphate, ammonium chloride, calcium chloride, arginine hydrochloride, zinc chloride, sodium acetate, amino acids or a combination thereof.

In one embodiment, the salt is sodium chloride or magnesium chloride, optionally in combination with other salts. In one embodiment, the salt is arginine hydrochloride. In one embodiment, the salt is a combination of an inorganic salt and arginine hydrochloride.

In one embodiment, the salt is an amino acid. In one embodiment the L-stereoisomer of the amino acid is used. In one embodiment, the salt selected from arginine, glycine, lysine, aspartic acid, or glutamic acid, or a combination thereof. In one embodiment, the amino acid is arginine or glycine. In a further embodiment, the amino acid is arginine, such as L-arginine. The amino acid can be added to the composition in its salt form or in its free form, whatever is suitable.

In one embodiment, the salt (or combination of salts) is present in a concentration of between 0 and 100 mM. In one embodiment, the total concentration of salt is 100 mM or lower, such as 50 mM, 40 mM, 35 mM, 33 mM, 30 mM, 25 mM or lower.

It has surprisingly been found that the amino acid, L-arginine, acts as a stabilizer, and that the presence of L-arginine has a statistically significant stabilising effect against the formation of HMWP aggregates in high concentration liquid formulations of proteins, such as antibodies. Thus, the invention also provides a stable liquid composition comprising an antibody and arginine at a concentration of between 5 mM and 100 mM, such as or lower, such as 50 mM, 40 mM, 35 mM, 33 mM, 30 mM, 25 mM or lower. In one embodiment, the buffer is a suitable pharmaceutically acceptable buffer, which comprises both a pharmaceutically acceptable base and a pharmaceutically acceptable acid. In one embodiment, the buffer has a pKa of between 4 and 8.

Examples of pharmaceutically acceptable acid and bases may include inorganic as well as organic non-toxic acid/bases such as it is well-known in the art. Examples are disodium acetate, sodium carbonate, citrate, glycylglycine, histidine, glycine, lysine, arginine, maleate, succinate, sodium dihydrogen phosphate, disodium hydrogen phosphate, sodium phosphate, and tris(hydroxymethyl)-amino methane, or mixtures thereof. Each one of these specific buffers constitutes an alternative embodiment of the invention. In one embodiment, the pharmaceutically acceptable buffer comprises histidine, maleate, succinate, phosphate, or tris(hydroxymethyl)-amino methane.

In one embodiment, the buffer has a pKa value ±1 pH unit from the target pH of the composition.

In one embodiment, the composition is buffered to a pH of between 5 and 7, such as a pH of 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0 or to a pH as defined by any ranges there between. In one embodiment, the composition is buffered to a pH of 5.0, 5.5, 6.0, 6.5 or 7.0. In one embodiment, the composition is buffered to a pH of between 6.0 and 6.5. In one embodiment, the composition is buffered to a pH of 6.0 or 6.5.

In one embodiment, the composition additionally comprises a surfactant. In one embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (eg. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (polysorbates, e.g. polysorbat 20, polysorbat 40, polysorbat 80 and Brij-35), monoglycerides or ethoxylated derivatives thereof, diglycerides or polyoxyethylene derivatives thereof, alcohols, glycerol, lectins and phospholipids (eg. phosphatidyl serine, phosphatidyl choline, phosphatidyl ethanolamine, phosphatidyl inositol, diphosphatidyl glycerol and sphingomyelin), derivates of phospholipids (eg. dipalmitoyl phosphatidic acid) and lysophospholipids (eg. palmitoyl lysophosphatidyl-L-serine and 1-acyl-sn-glycero-3-phosphate esters of ethanolamine, choline, serine or threonine) and alkyl, alkoxyl(alkyl ester), alkoxy(alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (eg. cephalins), glyceroglycolipids (eg. galactopyransoide), sphingoglycolipids (eg. ceramides, gangliosides), dodecylphosphocholine, hen egg lysolecithin, fusidic acid derivatives- (e.g. sodium tauro-dihydrofusidate etc.), long-chain fatty acids and salts thereof C6-C12 (eg. oleic acid and caprylic acid), acylcarnitines and derivatives, $N^\alpha$-acylated derivatives of lysine, arginine or histidine, or side-chain acylated derivatives of lysine or arginine, $N^\alpha$-acylated derivatives of dipeptides comprising any combination of lysine, arginine or histidine and a neutral or acidic amino acid, N$^\alpha$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulphate or sodium lauryl sulphate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quaternary ammonium bases) (e.g. cetyl-trimethylammonium bromide, cetylpyridinium chloride), non-ionic surfactants (eg. Dodecyl β-D-glucopyranoside), poloxamines (eg. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention. In one embodiment, the surfactant is polysorbate 80 (i.e. Tween™80).

The use of a surfactant in pharmaceutical compositions is well-known to the skilled person. For convenience reference is made to Remington: *The Science and Practice of Pharmacy*, 20$^{th}$ edition, 2000.

In one embodiment, the surfactant is present within the composition in an amount of below 0.01%. In one embodiment, the surfactant is present within the composition in an amount of below 0.0075%, i.e between 0.001% and 0.005%, such as 0.001%.

In one embodiment, no surfactant is present. Surprisingly, it has been found that compositions of protein can be stable with both low amounts of salt, low amount of buffer or low amount of salt and buffer and without any addition of surfactant.

In one embodiment, the composition additionally comprises a tonicity modifying agent. Examples of suitable tonicity modifying agents include salts (e.g sodium chloride), polyhydric alcohols (e.g propyleneglycol, glycerol, xyllitol, mannitol or D-sorbitol), monosaccarides (glucose or maltose), di saccarides (e.g sucrose), amino acids (L-glycine, L-histidine, arginine, lysine, isoleucine, aspartic acid, tryptophane, threonine), polyethylen glycols (e.g PEG 400) or mixtures thereof. In one embodiment, the tonicity modifying agent is sucrose, mannitol or propylene glycol. In a further embodiment, the tonicity modifying agent is sucrose. In some embodiments, the buffer and/or salt of the composition (as described above) also acts as tonicity modifier or the tonicity modifier will act as a buffer and/or salt (and the concentration of the tonicity modifier will therefore in such cases be calculated as such).

In one embodiment, the tonicity modifying agent is present within the composition in an amount of between 50 and 250 mM, such as between 100 and 200 mM, for example any one of 100, 110, 120, 130, 140, 150, 160, 170, 180, 190 or 200 or any ranges there between. In one embodiment, the tonicity modifying agent is present within the composition in an amount of 150 mM.

In one embodiment, the composition is isotonic.

In one embodiment, the protein is an immunoglobulin. In one embodiment, the protein is an antibody. In one embodiment, the protein is a monoclonal antibody (mAb). In one embodiment, the protein is an IgG4 antibody.

The term "antibody" covers monoclonal antibodies (including full length antibodies which have an immunoglobulin Fc region), antibody compositions with polyepitopic specificity, bispecific antibodies, diabodies, and single-chain molecules, as well as antibody fragments (e.g., Fab, F(ab')$_2$, and Fv).

The term "monoclonal antibody" as used herein refers to an antibody obtained from a population of substantially homogeneous antibodies, i. e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e. g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein may extend to include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)).

Examples of suitable antibodies, which may be formulated in a stable composition of the invention include: 3F8, Abagovomab, Abciximab, ACZ885 (canakinumab), Adalimumab, Adecatumumab, Afelimomab, Afutuzumab, Alacizumab pegol, Alemtuzumab, Altumomab pentetate, Anatumomab mafenatox, Anrukinzumab (IMA-638), Apolizumab, Arcitumomab, Aselizumab, Atlizumab (tocilizumab), Atorolimumab, Bapineuzumab, Basiliximab, Bavituximab, Bectumomab, Belimumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, ONTO 148 (golimumab), ONTO 1275 (ustekinumab), Conatumumab, Dacetuzumab, Daclizumab, Denosumab, Detumomab, Dorlimomab aritox, Dorlixizumab, Ecromeximab, Eculizumab, Edobacomab, Edrecolomab, Efalizumab, Efungumab, Elsilimomab, Enlimomab pegol, Epitumomab cituxetan, Epratuzumab, Erlizumab, Ertumaxomab, Etaracizumab, Exbivirumab, Fanolesomab, Faralimomab, Felvizumab, Fezakinumab, Figitumumab, Fontolizumab, Foravirumab, Fresolimumab, Galiximab, Gantenerumab, Gavilimomab, Gemtuzumab ozogamicin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, MYO-029 (stamulumab), Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO 140, Rafivirumab, Ramucirumab, Ranibizumab, Raxibacumab, Regavirumab, Reslizumab, Rilotumumab, Rituximab, Robatumumab, Rontalizumab, Rovelizumab, Ruplizumab, Satumomab, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, TGN1412, Ticilimumab (tremelimumab), Tigatuzumab, TNX-355 (ibalizumab), TNX-650, TNX-901 (talizumab), Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, Zolimomab aritox and the like.

In one embodiment, the antibody is a monoclonal anti-IL20 antibody. In one embodiment, the antibody is an anti-IL20 antibody as described in WO2010/000721. In one embodiment, the anti-IL20 monoclonal antibody is 15D2 or 5B7 as described in WO2010/000721.

In one embodiment, the antibody is a monoclonal anti-TFPI monoclonal antibody. In one embodiment, the antibody is an anti-TFPI antibody as described in PCT2009EP067598. In one embodiment, the anti-TFPI monoclonal antibody is HzTFPI4F36 as described in PCT2009EP067598.

SEQ ID NOs: 1-3 provide the sense polynucleotide, anti-sense polynucleotide and polypeptide sequences, respectively, for the light chain variable domain (VL) of the humanized monoclonal antibody, HzTFPI4F36 (mAbTFPI2021). Signal peptide sequences are omitted.

SEQ ID NOs: 4-6 provide the sense polynucleotide, anti-sense polynucleotide and polypeptide sequences, respectively, for the heavy chain variable domain (VH) of the humanized monoclonal antibody, HzTFPI4F36 (mAbTFPI2021).

SEQ ID NOs: 7-9 provide the sense polynucleotide, anti-sense polynucleotide and polypeptide sequences, respectively, for the light chain (LC) of the humanized monoclonal antibody, HzTFPI4F36 (mAbTFPI2021).

SEQ ID NOs: 10-12 provide the sense polynucleotide, anti-sense polynucleotide and polypeptide sequences, respectively, for the heavy chain (HC) of the humanized monoclonal antibody, HzTFPI4F36 (mAbTFPI2021). Signal peptide sequences are omitted.

In one embodiment, the antibody is a monoclonal anti-C5aR monoclonal antibody. In one embodiment, the antibody is an anti-C5aR antibody as described in WO2009/103113. In one embodiment, the anti-C5aR monoclonal antibody is 7F3 as described in WO2009/103113.

In one embodiment, the antibody is a monoclonal anti-NKG2D monoclonal antibody. In one embodiment, the antibody is an anti-NKG2D antibody as described in WO2009/077483. In one embodiment, the anti-NKG2D monoclonal antibody is MS as described in WO2009/077483.

In one embodiment, the antibody is a monoclonal anti-NKG2A monoclonal antibody. In one embodiment, the antibody is an anti-NKG2A antibody as described in WO2008/009545. In one embodiment, the anti-NKG2A monoclonal antibody is humZ270 as described in WO2008/009545.

It will be appreciated that the invention finds particular utility where the protein is present within the composition in high concentrations. Thus, in one embodiment, the protein is present in a concentration of 50 mg/ml or more, such as 55, 60, 65, 70, 75, 80, 85, 90, 95, 100, 150, 200, 250, 300 mg/ml or more. In one embodiment, the protein is present within the composition in an amount of between 50 mg/ml and 300 mg/ml, for instance between 50 mg/ml and 250 mg/ml, such as between 50 mg/ml and 200 mg/ml, for instance between 50 mg/ml and 150 mg/ml. In one embodiment, the protein is present in a concentration of between 75 mg/ml and 300 mg/ml, for instance between 75 mg/ml and 250 mg/ml, such as between 75 mg/ml and 200 mg/ml, for instance between 75 mg/ml and 150 mg/ml. In one embodiment, the protein is present in a concentration of between 100 mg/ml and 300 mg/ml, for instance between 100 mg/ml and 250 mg/ml, such as between 100 mg/ml and 200 mg/ml, for instance between 100 mg/ml and 150 mg/ml.

In one embodiment, the stable compositions of the invention have a viscosity of 50 cP or less when measured at 25° C., such as any of less than 45, 40, 35, 30, 25, 20, 15, 10, 5 or 1 cP. In particular, the stable compositions of the invention have a viscosity of 5 cP or less when measured at 25° C.

Employing a high concentrated formulation containing for instance 100 mg/ml protein and lower than 100 mM of the sum of salt and buffer concentration renders a relatively low-viscous formulation (5 cP at 25° C. for an anti-IL20 antibody) which is stable at storage temperature of 2-8° C. In one embodiment, the formulation is also stable at higher temperatures such as room temperature. The formulation is suitable for use in ready-to-use devices with a small needle size conferring enhanced patient convenience as compared to a marketed ready to use product (for instance Humira® which employs a 27G needle and 50 mg/ml of antibody concentration).

In one embodiment, a protein composition of the invention comprises:
(a) ≥50 mg/ml antibody;
(b) 30 mM or lower of a in-organic salt, such as sodium chloride or magnesium chloride;
(c) 0-25 mM of an amino acid, such as arginine or glycine;
(d) 50 mM or lower of a buffer such as histidine buffer;
(e) 0.001-0.005% of a non-ionic surfactant;
(f) 100-200 mM of a tonicity modifying agent, such as sucrose, propylene glycol, glycerol, mannitol or D-sorbitol;
buffered to a pH of between 5 and 7.

In one embodiment, a protein composition of the invention comprises:
(a) 100 mg/ml antibody;
(b) 25 mM sodium chloride;
(c) 33 mM histidine buffer;
(d) 25 mM arginine;
(e) 0.001% polysorbate 80;
(f) 150 mM sucrose;
buffered to a pH of between 5 and 7.

In one embodiment, the stable protein composition comprises:
(a) 100 mg/ml antibody;
(b) 25 mM sodium chloride;
(c) 33 mM histidine buffer;
(d) 25 mM arginine;
(e) 0.001% polysorbate 80;
(f) 150 mM mannitol;
buffered to a pH of between 5 and 7.

In one embodiment, the stable protein composition comprises:
(a) 100 mg/ml antibody;
(b) 25 mM sodium chloride;
(c) 33 mM histidine buffer;
(d) 25 mM arginine;
(e) 0.001% polysorbate 80;
(f) 150 mM sucrose;
buffered to a pH of 6.0 to 6.5.

In one embodiment, the stable protein composition comprises:
(a) 100 mg/ml antibody;
(b) 25 mM sodium chloride;
(c) 33 mM histidine buffer;
(d) 25 mM arginine;
(e) 150 mM sucrose;
buffered to a pH between 5 and 7.

Compositions of the invention have surprisingly demonstrated stability towards formation of HMWP at room temperature (here measured at 25° C.) for 12 months and at 5° C. for up to 24 months where there is no detectable increase of % HMWP. In addition, several compositions of the invention typically show that only 2-7% of HMWP is formed over 3 months at 40° C. suggesting an interesting thermostable formulation despite having a low total concentration of salt and buffer.

It will be apparent to those skilled in the art of pharmaceutical compositions that the stable protein compositions hereinbefore described may be prepared in accordance with standard procedures (Luo R et al. High-concentration UF/DF of a monoclonal antibody. Strategy for optimization and scale-up, Bioprocess Int. 4, 44-48 (2006)). For example, the stable protein compositions may typically be prepared by first dia-filtrating the protein at a concentration of 50 mg/ml or more by use of Tangential Flow Filtration (TFF). Subsequently, the formulated product, except for the addition of a surfactant (where applicable) is ultra-filtrated to 100 mg/ml or higher concentrations after which surfactant may be added.

It is possible that other ingredients may be present in the pharmaceutical composition of the present invention. Such additional ingredients may include cosolvents, wetting agents, emulsifiers, antioxidants, bulking agents, chelating agents, metal ions, oleaginous vehicles, proteins (e.g., human serum albumin, gelatine or proteins) and a zwitterion. Such additional ingredients, of course, should not adversely affect the overall stability of the pharmaceutical formulation of the present invention.

In one embodiment, the pharmaceutical compositions of the invention are stable for more than 6 weeks of usage and for more than 3 years of storage.

In one embodiment, the pharmaceutical compositions of the invention are stable for more than 4 weeks of usage and for more than 3 years of storage.

In one embodiment, the pharmaceutical compositions of the invention are stable for more than 4 weeks of usage and for more than two years of storage.

In one embodiment, the pharmaceutical compositions of the invention are stable for more than 2 weeks of usage and for more than two years of storage.

In one embodiment, the pharmaceutical compositions of the invention are stable for more than 1 week of usage and for more than six months of storage.

According to a second aspect of the invention, there is provided a stable protein composition as defined herein for use in therapy.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal; in particular a human being, but it may also include animals, such as dogs, cats, cows, sheep and pigs.

For example, the compositions of anti-IL20 antibodies of the present invention may be used in the treatment of an inflammatory disease, in particular autoinflammatory diseases, such as psoriasis, systemic lupus erythomatosus, rheumatoid arthritis, Crohn's disease and psoriatic arthritis or otherwise as described in WO2010/000721.

Thus according to a further aspect, the invention provides a method of treating such an inflammatory disease which comprises administering to a patient a therapeutically effective amount of a composition of an anti-IL20 antibody of the present invention.

The invention also provides a composition of an anti-IL20 antibody of the present invention for use in the treatment of such an inflammatory disease.

The invention also provides the use of a composition of an anti-IL20 antibody of the present invention in the manufacture of a medicament for the treatment of such an inflammatory disease.

The invention also provides a pharmaceutical composition comprising a composition of an anti-IL20 antibody of the present invention for use in the treatment of such an inflammatory disease.

For example, the compositions of anti-TFPI antibodies of the present invention may be used in the treatment of a coagulopathy (bleeding disorder), such as haemophilia A, with or without inhibitors, and haemophilia B, with or without inhibitors or otherwise as described in PCT2009EP067598.

Thus according to a further aspect, the invention provides a method of treating a coagulopathy which comprises administering to a patient a therapeutically effective amount of a composition of an anti-TFPI antibody of the present invention.

The invention also provides a composition of an anti-TFPI antibody of the present invention for use in the treatment of a coagulopathy.

The invention also provides the use of a composition of an anti-TFPI antibody of the present invention in the manufacture of a medicament for the treatment of a coagulopathy.

The invention also provides a pharmaceutical composition comprising a composition of an anti-IL20 antibody of the present invention for use in the treatment of a coagulopathy.

For example, the compositions of anti-C5aR antibodies of the present invention may be used in the treatment of an inflammatory disease, in particular autoinflammatory diseases, such as psoriasis, systemic lupus erythomatosus, rheumatoid arthritis, Crohn's disease and psoriatic arthritis or otherwise as described in WO2009/103113.

Thus according to a further aspect, the invention provides a method of treating an inflammatory disease which comprises administering to a patient a therapeutically effective amount of a composition of an anti-C5aR antibody of the present invention.

The invention also provides a composition of an anti-C5aR antibody of the present invention for use in the treatment of an inflammatory disease.

The invention also provides the use of a composition of an anti-C5aR antibody of the present invention in the manufacture of a medicament for the treatment of an inflammatory disease.

The invention also provides a pharmaceutical composition comprising a composition of an anti-C5aR antibody of the present invention for use in the treatment of an inflammatory disease.

For example, the compositions of anti-NKG2D antibodies of the present invention may be used in the treatment of an inflammatory disease, in particular autoinflammatory diseases, such as psoriasis, systemic lupus erythomatosus, rheumatoid arthritis, Crohn's disease and psoriatic arthritis or otherwise as described in WO2009/077483.

Thus according to a further aspect, the invention provides a method of treating an inflammatory disease which comprises administering to a patient a therapeutically effective amount of a composition of an anti-NKG2D antibody of the present invention.

The invention also provides a composition of an anti-NKG2D antibody of the present invention for use in the treatment of an inflammatory disease.

The invention also provides the use of a composition of an anti-NKG2D antibody of the present invention in the manufacture of a medicament for the treatment of an inflammatory disease.

The invention also provides a pharmaceutical composition comprising a composition of an anti-NKG2D antibody of the present invention for use in the treatment of an inflammatory disease.

For example, the compositions of anti-NKG2A antibodies of the present invention may be used in the treatment of an inflammatory disease, in particular autoinflammatory (also called autoimmune) diseases, such as psoriasis, systemic lupus erythomatosus, rheumatoid arthritis, Crohn's disease and psoriatic arthritis or otherwise as described in WO2008/009545.

Thus according to a further aspect, the invention provides a method of treating an inflammatory disease which comprises administering to a patient a therapeutically effective amount of a composition of an anti-NKG2A antibody of the present invention.

The invention also provides a composition of an anti-NKG2A antibody of the present invention for use in the treatment of an inflammatory disease.

The invention also provides the use of a composition of an anti-NKG2A antibody of the present invention in the manufacture of a medicament for the treatment of an inflammatory disease.

The invention also provides a pharmaceutical composition comprising a composition of an anti-NKG2A antibody of the present invention for use in the treatment of an inflammatory disease.

It is to be understood, that therapeutic and prophylactic (preventive) regimes represent separate aspects of the present invention.

The pharmaceutical formulations of the invention are generally suitable for parenteral administration. Parenteral administration may be performed by subcutaneous, intramuscular, intraperitoneal or intravenous injection by means of a syringe, optionally a pen-like syringe. Alternatively, parenteral administration can be performed by means of an infusion pump.

The invention is further described with reference to the following non-limiting examples.

EXAMPLES

Example 1

18 formulations were prepared (see below Table 1). The formulations were prepared from a stock solution containing ca. 150 mg/ml of the mAb 1 and 10 mM histidine buffer, pH 6.5. This stock solution was prepared by conventional UF/DF/UF. Stock solution of the excipients were prepared and mixed in the correct proportion using a Biomek® 2000, Beckman Coulter robot system. The final formulations were filled in 3 ml Penfill® cartridges, type 1 glass. The piston in the cartridge was adjusted to accommodate 0.6 ml which was also the filling volume. The formulations were stored at 40° C. for three months and then analysed chemically, pharmaceutical chemically and biophysically. The increase in the formation of protein aggregates (% HMWP) can be modelled using SAS JMP 8.0 software. The data show that there is a positive effect on the stability of arginine which decreased the formation of protein aggregates significantly. Similarly, the combined effect of histidine and NaCl also decreases the formation of protein aggregates. Sucrose and Polysorbate 80 (PS 80) weakly augments the formation of protein aggregates.

TABLE 1

Composition of formulations

| mAb 1 (mg/ml) | Histidine (mM) | NaCl (mM) | PS 80 (mg/ml) | Sucrose (mM) | Arginine (mM) | pH | % ΔHMWP |
|---|---|---|---|---|---|---|---|
| 100 | 33 | 25 | 0.01 | 0 | 25 | 6.5 | 1.4 |
| 100 | 66 | 25 | 0.01 | 0 | 0 | 6.5 | 2.1 |
| 100 | 33 | 100 | 0.01 | 0 | 0 | 6.5 | 2.0 |
| 100 | 66 | 100 | 0.01 | 0 | 25 | 6.5 | 1.7 |
| 100 | 33 | 25 | 0.05 | 0 | 0 | 6.5 | 2.3 |
| 100 | 66 | 25 | 0.05 | 0 | 25 | 6.5 | 1.8 |
| 100 | 33 | 100 | 0.05 | 0 | 25 | 6.5 | 1.8 |
| 100 | 66 | 100 | 0.05 | 0 | 0 | 6.5 | 1.8 |
| 100 | 33 | 25 | 0.01 | 30 | 0 | 6.5 | 2.6 |
| 100 | 66 | 25 | 0.01 | 30 | 25 | 6.5 | 1.7 |
| 100 | 33 | 100 | 0.01 | 30 | 25 | 6.5 | 1.6 |
| 100 | 66 | 100 | 0.01 | 30 | 0 | 6.5 | 1.6 |
| 100 | 33 | 25 | 0.05 | 30 | 25 | 6.5 | 1.5 |
| 100 | 66 | 25 | 0.05 | 30 | 0 | 6.5 | 3.6 |
| 100 | 33 | 100 | 0.05 | 30 | 0 | 6.5 | 3.6 |
| 100 | 66 | 100 | 0.05 | 30 | 25 | 6.5 | 1.9 |
| 100 | 49.5 | 62.5 | 0.03 | 15 | 12.5 | 6.5 | 1.8 |
| 100 | 49.5 | 62.5 | 0.03 | 15 | 12.5 | 6.5 | 1.8 |

PS = polysorbate

Figure 1:
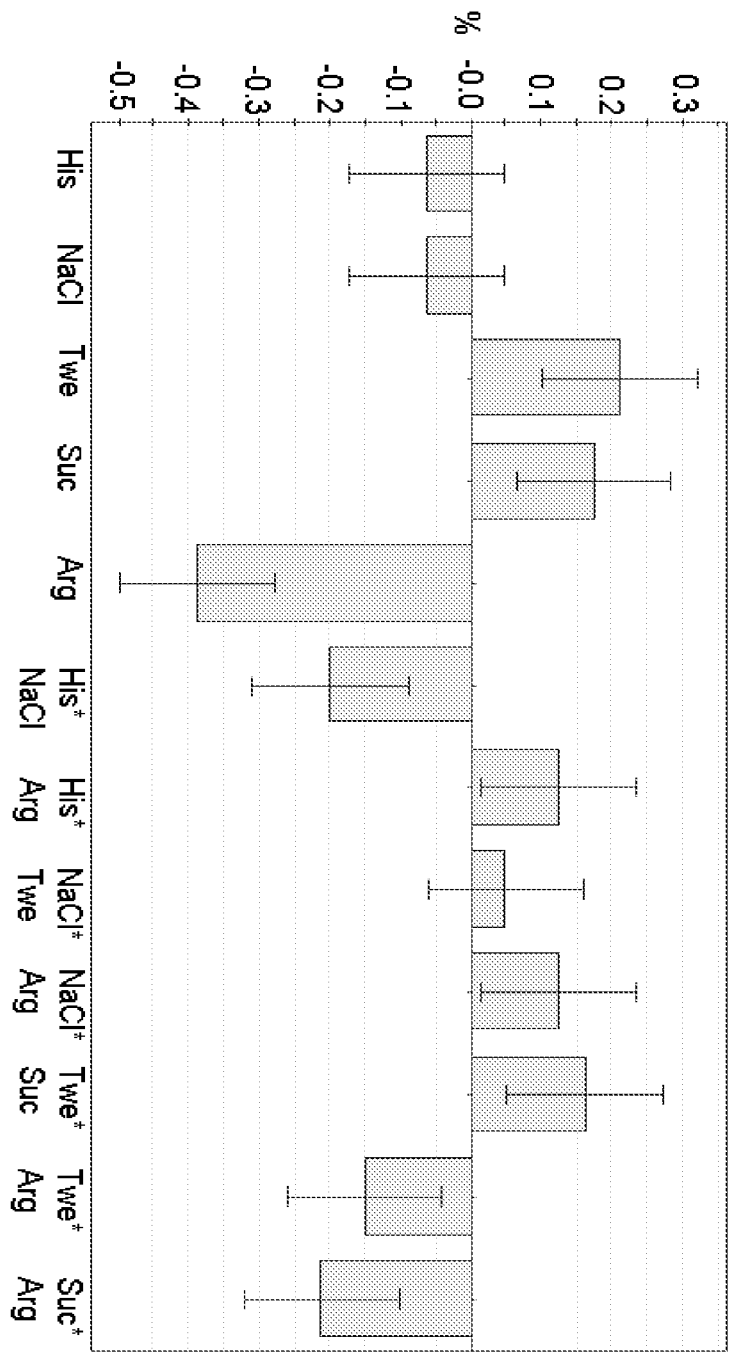
FIG. 1. shows a statistical analysis of the effect of main factors and 2-factors interactions on the formation of % HMWP after the formulations have been stored at 40° C. for 3 months.

The statistical effect of main factors and 2-factors interactions on the formation of % HMWP, after the formulation has been stored at 40° C. for three months is shown in FIG. 1.

Example 2

A mAb-solution is prepared by UF/DF/UF to a concentration >100 mg/ml including either 10 mM histidine or 10 mM NaCl. A solution containing the excipients to be investigated is prepared and mixed with the mAb-solution to the aimed concentration. pH is adjusted to the aimed pH. The formulations were filled in 3 ml Penfill® cartridges, type 1 glass. The piston in the cartridge was adjusted to accommodate 1.5 ml which was also the filling volume. The cartridges were stored at 5° C. and/or 25° C. and/or 40° C. Table 2 shows the various formulations prepared and the resulting viscosity and increase in aggregates (% HMWP).

Similar to Example 1 it is observed that arginine has an stabilising effect as it counteracts the formation of % HMWP. Histidine is also observed to contain similar stabilising effect. Furthermore, it was also observed that histidine, sodium chloride and arginine each have a statistically significant viscosity-lowering effect on the formulation—histidine having the most profound effect.

Interestingly, after 12 months at 25° C. the increase in % HMWP is virtually non-existing which strongly indicates that there is a potential for a room temperature stable formulation (Table 2).

mAb1 is the 15D2 anti-IL20 antibody as described in WO2010/000721. mAb2 is the anti-TFPI monoclonal antibody HzTFPI4F36 as described in PCT2009EP067598. mAb3 is the anti-C5aR monoclonal antibody hAb-Q as described in WO2009/103113. mAb4 is the anti-NKG2D monoclonal antibody MS as described in 2009/077483. mAb5 is the anti-NKG2A monoclonal antibody humZ270 as described in WO2008/009545

TABLE 2

Examples of formulations and their corresponding viscosity and chemical stability

| mAb | Conc of mAb (mg/ml) | Composition | Storage temp (° C.) | Storage time (months) | ΔHMWP (%) | Viscosity (cP) |
|---|---|---|---|---|---|---|
| mAb1 | 100 | Histidine 33 mM NaCl 25 mM PS 80 0.001% Arginine 25 mM pH 6.5 | 5 5 25 40 | 12 24 3 3 | 0.0 0.0 0.2 1.4 | 5.4 |
| mAb1 | 50 | Histidine 33 mM NaCl 25 mM PS 80 0.001% Arginine 25 mM pH 6.5 | 5 40 | 18 3 | 0.3 3.1 | 3.7 |
| mAb1 | 100 | Histidine 66 mM NaCl 25 mM PS 80 0.001% pH 6.5 | 5 5 25 40 | 12 24 3 3 | 0.1 0.0 0.3 2.1 | 5.9 |
| mAb1 | 100 | Histidine 33 mM NaCl 25 mM PS 80 0.005% pH 6.5 | 5 5 25 40 | 12 24 3 3 | 0.3 0.0 0.5 2.3 | 5.5 |
| mAb1 | 100 | Histidine 33 mM NaCl 25 mM PS 80 0.001% Sucrose 30 mM pH 6.5 | 5 5 25 40 | 12 24 3 3 | 0.0 0.0 0.4 2.6 | 5.4 |
| mAb1 | 50 | Histidine 33 mM NaCl 25 mM PS 80 0.005% Sucrose 30 mM Arginine 25 mM pH 6.5 | 5 40 | 18 3 | 0.2 3.4 | 2.3 |
| mAb1 | 100 | Histidine 33 mM NaCl 25 mM Arginine 25 mM PS 80 0.001% Sucrose 150 mM pH 6.5 | 5 15 25 30 40 | 12 12 12 12 12 | 0.0 0.1 0.2 0.5 13.8 | 5.9 |

TABLE 2-continued

Examples of formulations and their corresponding viscosity and chemical stability

| mAb | Conc of mAb (mg/ml) | Composition | Storage temp (° C.) | Storage time (months) | ΔHMWP (%) | Viscosity (cP) |
|---|---|---|---|---|---|---|
| mAb1 | 100 | Histidine 10 mM<br>PS 80 0.001%<br>Arginine 70 mM<br>pH 6.5 | 40 | 3 | 2.8 | 6.7 |
| mAb1 | 100 | Histidine 10 mM<br>NaCl 70 mM<br>PS 80 0.001%<br>pH 6.5 | 40 | 3 | 3.6 | 7.1 |
| mAb1 | 100 | Histidine 10 mM<br>pH 6.5 | 5<br>40 | 18<br>3 | 0.0<br>6.1 | 9.3 |
| mAb1 | 150 | Histidine 33 mM<br>NaCl 25 mM<br>PS 80 0.001%<br>Arginine 25 mM<br>pH 6.5 | 5<br>25<br>40 | 12<br>3<br>3 | 0.0<br>0.0<br>4.0 | 6.0 |
| mAb1 | 100 | Na-phosphate 10 mM<br>NaCl 25 mM<br>PS 80 0.005%<br>Arginine 25 mM<br>pH 6.5 | 40 | 3 | 3.7 | 4.2 |
| mAb1 | 100 | Succinate 10 mM<br>NaCl 25 mM<br>PS 80 0.005%<br>Arginine 25 mM<br>pH 6.5 | 40 | 3 | 2.8 | 5.6 |
| mAb1 | 100 | Na-citrate 10 mM<br>NaCl 25 mM<br>PS 80 0.005%<br>Arginine 25 mM<br>pH 6.5 | 40 | 3 | 2.4 | 8.7 |
| mAb1 | 100 | Maleate 10 mM<br>NaCl 25 mM<br>PS 80 0.005%<br>Arginine 25 mM<br>pH 6.51.7 | 40 | 3 | 2.9 | 4.8 |
| mAb1 | 100 | Tris (hydrxy-methyl-amino-methan) 10 mM<br>NaCl 25 mM<br>PS 80 0.005%<br>Arginine 25 mM<br>pH 6.5 | 40 | 3 | 2.5 | 3.9 |
| mAb2 | 150 | Histidine 33 mM<br>NaCl 25 mM<br>PS 80 0.001%<br>Arginine 25 mM<br>pH 6.0 | 40<br>40<br>5 | 1<br>3<br>12 | 1.1<br>3.7<br>0.1 | 10.0 |
| mAb2 | 100 | Histidine 33 mM<br>NaCl 25 mM<br>PS 80 0.001%<br>Arginine 25 mM<br>pH 6.0 | 40<br>40<br>5 | 1<br>3<br>12 | 0.7<br>2.9<br>0.0 | 6.6 |
| mAb2 | 150 | Histidine 10 mM<br>pH 6.0 | 40<br>40<br>5 | 1<br>3<br>12 | 1.4<br>4.5<br>0.1 | 8.6 |
| mAb2 | 100 | Histidine 10 mM<br>pH 6.0 | 40<br>40<br>5 | 1<br>3<br>12 | 0.9<br>3.3<br>0.0 | 9.5 |
| mAb3 | 100 | Histidine 50 mM<br>NaCl 25 mM<br>PS 80 0.005%<br>pH 6.5 | 5<br>5<br>40 | 6<br>18<br>3 | 0.3<br>0.1<br>3.7 | 5.6 |
| mAb3 | 100 | Histidine 25 mM<br>NaCl 25 mM<br>PS 80 0.001%<br>pH 6.5 | 5<br>5<br>40 | 6<br>18<br>3 | 0.8<br>1.3<br>5.3 | 6.5 |
| mAb3 | 100 | Histidine 10 mM<br>NaCl 25 mM<br>pH 6.5 | 5<br>5<br>40 | 6<br>18<br>2 | 0.6<br>1.3<br>2.8 | 7.1 |

TABLE 2-continued

Examples of formulations and their corresponding viscosity and chemical stability

| mAb | Conc of mAb (mg/ml) | Composition | Storage temp (° C.) | Storage time (months) | ΔHMWP (%) | Viscosity (cP) |
|---|---|---|---|---|---|---|
| mAb4 | 100 | Histidine 33 mM NaCl 25 mM PS 80 0.001% Sucrose 150 mM Arginine 25 mM pH 6.0 | 40 40 5 | 2 3 12 | 0.9 1.6 0.3 | 4.3 |
| mAb4 | 100 | Histidine 10 mM pH 6.0 | 40 40 5 | 2 3 12 | 3.4 4.8 0.5 | 4.3 |
| mAb5 | 100 | Histidine 33 mM NaCl 25 mM PS 80 0.001% Sucrose 150 mM Arginine 25 mM pH 6.0 | 5 40 | 9 3 | 0.0 3.1 | 6.5 |
| mAb5 | 100 | Histidine 10 mM pH 6.0 | 5 40 | 9 3 | 0.2 7.4 | 7.3 |

Figure 2:
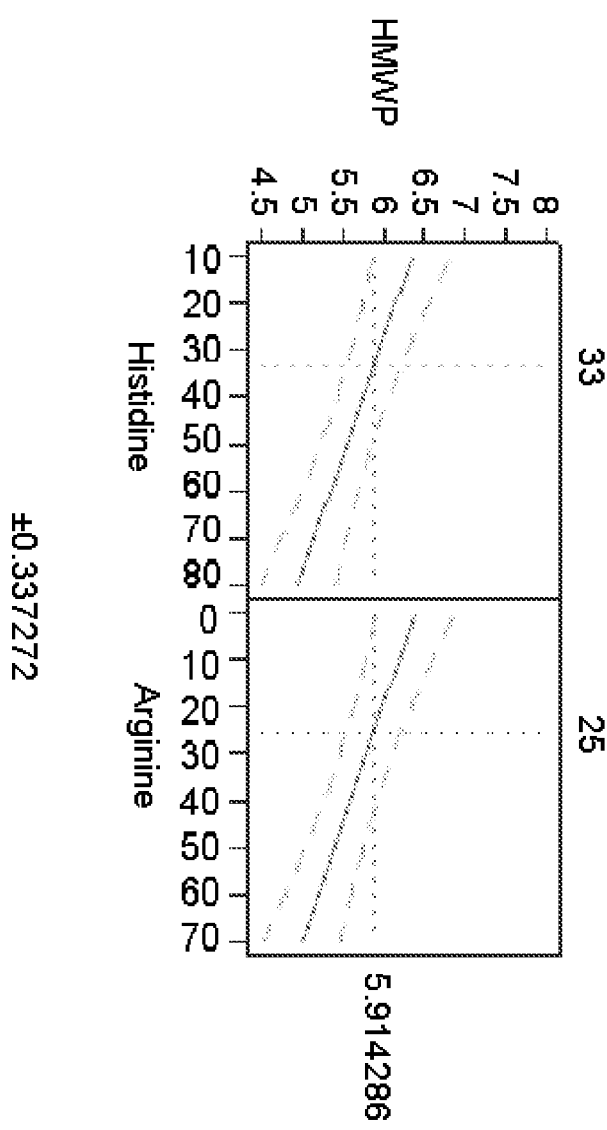
FIG. 2. shows the statistical analysis of the effect of histidine and arginine on the formulation of % HMWP after formulations have been stored at 40° C. for 3 months.

Conc. of mAb: the concentration of the stated antibody given in mg/ml.
ΔHMWP (%): Determined by SE-HPLC.
Viscosity: (cP) at 25° C. at time zero
PS: polysorbate The statistical effects of histidine og arginine on the formation of % HMWP after the formulation has been stored at 40° C. for 3 months, is shown in FIG. 2.

Figure 3:
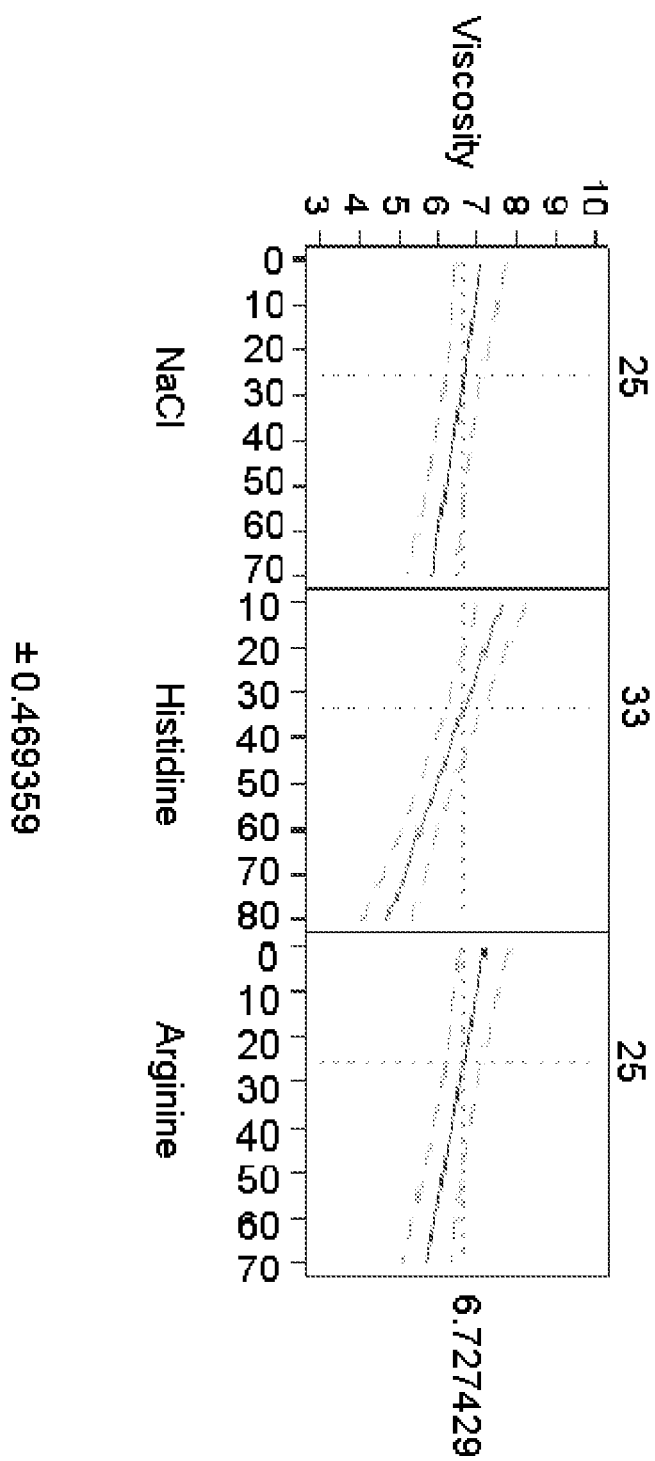
FIG. 3. shows the statistical analysis of the effect of histidine, sodium chloride (NaCl) and arginine on the viscosity of the formulation.

The statiscial effects of histidine, sodium chloride (NaCl) and arginine on the viscosity of the formulation is shown in FIG. 3.

Example 3

Formulations of mAbs have been prepared as mentioned in Example 2 with variation only in the amount of surfactant. The robustness of the formulations have been assessed by storage stability at accelerated and storage temperature (Table 3), and furthermore by mechanical agitation and freeze/thaw (Table 4). All formulations contain:

100 mg/ml mAb, 33 mM histidine, 25 mM arginine, 25 mM NaCl. 150 mM sucrose, 0-0.1 mg/ml Polysorbate 80. Formulation pH: 6.5 (mAb 1) and 6.0 (mAb 4)

TABLE 3

Storage stability at accelerated and storage temperature conditions. Formulations contain varying amounts of surfactant.

| mAb | Surfactant concentration (mg/ml) | Storage temp (° C.) | Storage time (months) | ΔHMWP* (%) | ΔTurbidity units* at 340 nm | Viscosity (cP) |
|---|---|---|---|---|---|---|
| mAb 1 | None | 5 | 9 | 0.0 | 0.02 | 6.0 |
|  |  | 40 | 3 | 1.6 | 0.26 |  |
| mAb 1 | 0.01 | 5 | 9 | 0.0 | 0.00 | 6.5 |
|  |  | 40 | 3 | 1.6 | 0.19 |  |
| mAb 1 | 0.02 | 5 | 9 | 0.0 | 0.00 | 6.4 |
|  |  | 40 | 3 | 1.6 | 0.25 |  |
| mAb 1 | 0.05 | 5 | 9 | 0.0 | 0.00 | 6.1 |
|  |  | 40 | 3 | 1.5 | 0.17 |  |
| mAb 1 | 0.1 | 5 | 9 | 0.0 | 0.00 | 6.0 |
|  |  | 40 | 3 | 1.7 | 0.34 |  |
| mAb 4 | None | 5 | 9 | 0.2 | 0.01 | 4.3 |
|  |  | 40 | 3 | 3.0 | 0.29 |  |
| mAb 4 | 0.01 | 5 | 9 | 0.1 | 0.03 | 4.9 |
|  |  | 40 | 3 | 3.0 | 0.32 |  |
| mAb 4 | 0.02 | 5 | 9 | 0.1 | 0.01 | 4.6 |
|  |  | 40 | 3 | 3.1 | 0.32 |  |

TABLE 3-continued

Storage stability at accelerated and storage temperature conditions. Formulations contain varying amounts of surfactant.

| mAb | Surfactant concentration (mg/ml) | Storage temp (° C.) | Storage time (months) | ΔHMWP* (%) | ΔTurbidity units* at 340 nm | Viscosity (cP) |
|---|---|---|---|---|---|---|
| mAb 4 | 0.05 | 5 | 9 | 0.2 | 0.01 | 5.0 |
|  |  | 40 | 3 | 3.3 | 0.36 |  |
| mAb 4 | 0.1 | 5 | 9 | 0.3 | 0.09 | 5.4 |
|  |  | 40 | 3 | 3.3 | 0.43 |  |

*The values are calculated as: time point X minus time point zero. Viscosity measued at 25° C. at time zero.

Visual appearance analysis has also been performed in light cabinet and architect lamp for all formulations to assess the possibility of formation of particles. At time zero all samples were found to be clear to slightly opalescent without any visible particles using both analytical methods. No difference has been observed during the storage stability period of the appearance of all formulations.

TABLE 4

Formulations of mAbs exposed to i) freeze-thaw stress (10 cycles from −20° C. to ambient temperature) ii) mechanical agitation at ambient temperature, and iii) combined rotation and thermal stress (37° C.)

| mAb | Surfactant conc. (mg/ml) | Freeze-thaw cycles ΔTurbidity units* at 340 nm | Mechanical agitation ΔTurbidity units* at 340 nm | Rotation and thermal stress ΔTurbidity units* at 340 nm |
|---|---|---|---|---|
| mAb 1 | None | 0.05 | 0.00 | 0.11 |
| mAb 1 | 0.01 | 0.00 | 0.00 | 0.00 |
| mAb 1 | 0.02 | 0.00 | 0.00 | 0.00 |
| mAb 1 | 0.05 | 0.00 | 0.00 | 0.00 |
| mAb 1 | 0.1 | 0.06 | 0.00 | 0.06 |
| mAb 4 | None | 0.06 | 0.00 | 0.07 |
| mAb 4 | 0.01 | 0.05 | 0.01 | 0.07 |
| mAb 4 | 0.02 | 0.18 | 0.00 | 0.05 |
| mAb 4 | 0.05 | 0.15 | 0.08 | 0.07 |
| mAb 4 | 0.1 | NA | 0.15 | 0.14 |

*The values are calculated as: time point X minus time point zero. Viscosity measued at 25° C. at time zero.

Visual appearance analysis has also been performed in light cabinet and architect lamp for all formulations to assess the possibility of formation of particles. At time zero all samples were found to be clear to slightly opalescent without any visible particles using both analytical methods. No difference has been observed during the above stress conditions. Furthermore, no increase in % HMWP could be detected during these stress conditions.

Example 4

Two batches (ca. 3 L) have been produced in pilot plant facility according to regular fill finish conditions. The formulation was filled in 3 ml Penfill® cartridges, type 1 glass. The piston in the cartridge was adjusted to accommodate 1 ml which was also the filling volume. The difference between the composition of the batches is that one contains Polysorbate 80 whereas the other does not. The two drug products are exposed to accelerated temperature conditions and mechanical agitation (Table 5).

TABLE 5

Storage stability of two pilot production batches of mAb 1.

| Composition (+/−PS 80) | Storage temp (° C.) | Storage time (months) | ΔHMWP* (%) | ΔTurbidity units* at 340 nm | Viscosity (cP) |
|---|---|---|---|---|---|
| Histidine 33 mM | 5 | 3 | 0.3 | 0.00 | 3.5 |
| NaCl 25 mM | 25 | 3 | 0.6 | 0.00 |  |
| Sucrose 150 mM | 30 | 3 | 0.4 | 0.00 |  |
| Arginine 25 mM | 40 | 3 | 2.1 | 0.46 |  |
| pH 6.5 | Ambient temperature** | 0.5 | 0.3 | 0.00 |  |
| Histidine 33 mM | 5 | 3 | 0.3 | 0.00 | 3.4 |
| NaCl 25 mM | 25 | 3 | 0.6 | 0.00 |  |
| Sucrose 150 mM | 30 | 3 | 0.4 | 0.00 |  |
| Arginine 25 mM | 40 | 3 | 2.5 | N.A |  |
| PS 80 0.001% | Ambient | 0.5 | 0.3 | 0.00 |  |
| pH 6.5 | temperature** |  |  |  |  |

*The values are calculated as: time point X minus time point zero. NA: not applicable. Viscosity measued at 25° C. at time zero.
**Mechanical agitation of drug product taking place at ambient temperature for 2 weeks.

Example 5

A lab scale batch was prepared as in Example 2 and filled in 3.0 ml Penfill® cartridges, type 1 glass. The piston in the cartridge was adjusted to accommodate 1.5 ml which was also the filling volume. The effect of air/water interfacial stress on the drug product was assessed by applying varying volume of air to the formulation, and exposing it to severe temperature and mechanical stress conditions (Table 6)

TABLE 6

Influence on protein stability of volume of air added to drug product filled in 3.0 ml Penfill ® cartridges*. Protein stability was assessed after rotational and thermal stress at 37° C. for 14 days.

| Volume of air added to drug product (µL) | % ΔHMWP** | ΔTurbidity units** at 340 nm |
|---|---|---|
| 0 | 0.0 | 0.11 |
| 25 | 0.0 | 0.12 |
| 50 | 0.0 | 0.12 |
| 100 | 0.1 | 0.13 |

*Drug product contains: 100 mg/ml mAb 1, 33 mM histidine, 25 mM arginine, 25 mM NaCl, 150 mM sucrose, 0.001% Polysorbate 80.
**The values are calculated as: time point X minus time point zero The following is a non-limiting list of embodiments of the present invention.

Embodiment 1: A stable, liquid composition comprising a protein, a salt and/or a buffer, characterised in that the total concentration of said salt and buffer is lower than 100 mM.

Embodiment 2: A composition according to embodiment 1, wherein the total concentration of said salt and buffer is between 5 and 100 mM.

Embodiment 3: A composition according to embodiment 1 or 2, wherein the total concentration of salt and buffer is between 5 and 95 mM.

Embodiment 4: A composition according to any of embodiments 1 to 3, wherein the total concentration of salt and buffer is between 5 and 90 mM.

Embodiment 5: A composition according to any of embodiments 1 to 4, wherein the total concentration of salt and buffer is between 5 and 85 mM.

Embodiment 6: A composition according to any of embodiments 1 to 5, wherein the total concentration of salt and buffer is between 5 and 80 mM.

Embodiment 7: A composition according to any of embodiments 1 to 6, wherein the total concentration of salt and buffer is between 5 and 75 mM.

Embodiment 8: A composition according to any of embodiments 1 to 7, wherein the total concentration of salt and buffer is between 5 and 70 mM.

Embodiment 9: A composition according to any of embodiments 1 to 8, wherein the total concentration of salt and buffer is between 5 and 65 mM.

Embodiment 10: A composition according to any of embodiments 1 to 9, wherein the total concentration of salt and buffer is between 5 and 60 mM.

Embodiment 11: A composition according to any of embodiments 1 to 10, wherein the total concentration of salt and buffer is between 5 and 55 mM.

Embodiment 12: A composition according to any of embodiments 1 to 11, wherein the total concentration of salt and buffer is between 5 and 50 mM.

Embodiment 13: A composition according to any of embodiments 1 to 12, wherein the total concentration of salt and buffer is between 5 and 45 mM.

Embodiment 14: A composition according to any of embodiments 1 to 13, wherein the total concentration of salt and buffer is between 5 and 40 mM.

Embodiment 15: A composition according to any of embodiments 1 to 14, wherein the total concentration of salt and buffer is between 5 and 35 mM.

Embodiment 16: A composition according to any of embodiments 1 to 15, wherein the total concentration of salt and buffer is between 5 and 30 mM.

Embodiment 17: A composition according to any of embodiments 1 to 16, wherein the total concentration of salt and buffer is between 5 and 25 mM.

Embodiment 18: A composition according to embodiment 1 or 2, wherein the concentration of the buffer is 100 or lower.

Embodiment 19: A composition according to any of embodiments 1 to 12, wherein the concentration of the buffer is 50 or lower.

Embodiment 20: A composition according to any of embodiments 1 to 13, wherein the concentration of the buffer is 45 or lower.

Embodiment 21: A composition according to any of embodiments 1 to 14, wherein the concentration of the buffer is 40 or lower.

Embodiment 22: A composition according to any of embodiments 1 to 15, wherein the concentration of the buffer is 35 or lower.

Embodiment 23: A composition according to embodiment 22, wherein the concentration of the buffer is 33 mM or lower.

Embodiment 24: A composition according to embodiment 1 or 2, wherein the concentration of the salt is 100 or lower.

Embodiment 25: A composition according to any of embodiments 1 to 12, wherein the concentration of the salt is 50 or lower.

Embodiment 26: A composition according to any of embodiments 1 to 13, wherein the concentration of the salt is 45 or lower.

Embodiment 27: A composition according to any of embodiments 1 to 14, wherein the concentration of the salt is 40 or lower.

Embodiment 28: A composition according to any of embodiments 1 to 15, wherein the concentration of the salt is 35 or lower.

Embodiment 29: A composition according to any of embodiments 1 to 16, wherein the concentration of the salt is 25 mM or lower.

Embodiment 30: A composition according to any embodiments 1 to 29, wherein a buffer is present, and the buffer has a pKa between 4 to 8.

Embodiment 31: A composition according to embodiment 30, wherein the buffer has a pKa between 5 to 7.

Embodiment 32: A composition according to any of embodiments 1 to 30, wherein a buffer is present, and the buffer is dosodium acetate, sodium carbonate, citrate, glycylglycine, histidine, glycine, lysine, arginine, maleate, succinate, sodium dihydrogen phosphate, disodium hydrogen phosphate, sodium phosphate, or tris(hydroxymethyl)-amino methane, or mixtures thereof.

Embodiment 33: A composition according to embodiment 32, wherein the buffer is histidine, maleate, succinate, phosphate, or tris(hydroxymethyl)-amino methane.

Embodiment 34: A composition according to embodiment 33, wherein the buffer is histidine.

Embodiment 35: A composition according any of embodiments 1-34, wherein the buffer has a pKa value ±1 pH unit from the target pH of the composition.

Embodiment 36: A composition according to any of embodiments 1 to 35, wherein a salt is present and the salt is selected from the group consisting of sodium chloride, magnesium chloride, sodium thiocyanate, ammonium thiocyanate, ammonium sulphate, ammonium chloride, calcium chloride, arginine hydrochloride, zinc chloride and sodium acetate or any combination thereof.

Embodiment 37: A composition according to embodiment 36, wherein the salt is sodium chloride or magnesium chloride.

Embodiment 38: A composition according to embodiment 37, wherein the salt is sodium chloride.

Embodiment 39: A composition according to embodiment 36, wherein the salt is arginine-HCl.

Embodiment 40: A stable, liquid composition comprising an antibody and arginine, wherein the arginine is present in a concentration of between 5 mM and 100 mM.

Embodiment 41: A composition according to embodiment 40, wherein the arginine is present in a concentration of between 5 mM and 50 mM.

Embodiment 42: A composition according to embodiment 41, wherein the arginine is present in a concentration of between 5 mM and 40 mM.

Embodiment 43: A composition according to embodiment 42, wherein the arginine is present in a concentration of between 5 mM and 35 mM.

Embodiment 44: A composition according to embodiment 43, wherein the arginine is present in a concentration of between 5 mM and 33 mM.

Embodiment 45: A composition according to embodiment 44, wherein the arginine is present in a concentration of between 5 mM and 30 mM.

Embodiment 46: A composition according to embodiment 45, wherein the arginine is present in a concentration of between 5 mM and 25 mM.

Embodiment 47: A composition according to embodiment 40 or embodiment 41, wherein the arginine is present in a concentration of 50 mM, 40 mM, 35 mM, 33 mM, 30 mM or 25 mM.

Embodiment 48: A composition according to any of embodiments 1 to 47, which has a pH of between 5.0 and 7.0.

Embodiment 49: A composition according to any of embodiments 1 to 48, which has a pH of 6.0 or 6.5.

Embodiment 50: A composition according to any of embodiments 1 to 49, which additionally comprises a surfactant.

Embodiment 51: A composition according to embodiment 50, wherein the surfactant is polysorbate 80.

Embodiment 52: A composition according to embodiment 50 or embodiment 51, wherein the surfactant is present within the composition in an amount of below 0.01%.

Embodiment 53: A composition according to any of embodiments 50 to 52, wherein the surfactant is present within the composition in an amount of below 0.0075%.

Embodiment 54: A composition according to any of embodiments 50 to 52, wherein the surfactant is present within the composition in an amount between 0.001% and 0.005%.

Embodiment 55: A composition according to any of embodiments 50 to 54, wherein the surfactant is present within the composition in an amount of 0.001%.

Embodiment 56: A composition according to any of embodiments 1 to 49, which does not comprise a surfactant.

Embodiment 57: A composition according to any of embodiments 1 to 56, which additionally comprises a tonicity modifying agent.

Embodiment 58: A composition according to embodiment 57, wherein the tonicity modifying agent is sucrose or mannitol.

Embodiment 59: A composition according to embodiment 58, wherein the tonicity modifying agent is sucrose.

Embodiment 60: A composition according to any of embodiments 57 to 59, wherein the tonicity modifying agent is present within the composition in an amount of between 50 and 250 mM.

Embodiment 61: A composition according to any of embodiments 57 to 60, wherein the tonicity modifying agent is present within the composition in an amount of between 100 and 200 mM.

Embodiment 62: A composition according to any of embodiments 57 to 61, wherein the tonicity modifying agent is present in an amount of 150 mM.

Embodiment 63: A composition according to any of embodiments 1 to 62, wherein the composition is pharmaceutically acceptable.

Embodiment 64: A composition according to any of embodiments 1 to 63, wherein the protein is an immunoglobulin.

Embodiment 65: A composition according to embodiment 64, wherein the protein is an antibody.

Embodiment 66: A composition according to any of embodiments 1 to 65, wherein the protein is present within the composition in a concentration of between 50 mg/ml and 300 mg/ml.

Embodiment 67: A composition according to embodiment 66, wherein the protein is present within the composition in a concentration of between 75 mg/ml and 300 mg/ml.

Embodiment 68: A composition according to embodiment 67, wherein the protein is present within the composition in a concentration of between 100 mg/ml and 300 mg/ml.

Embodiment 69: A composition according to embodiment 68, wherein the protein is present within the composition in a concentration of between 50 mg/ml and 200 mg/ml.

Embodiment 70: A composition according to embodiment 69, wherein the protein is present within the composition in a concentration of 50, 55, 60, 65, 70, 75, 80, 85, 90, 95, 100, 150, 200, 250, or 300 mg/ml.

Embodiment 71: A composition according to any of embodiments 1 to 70, which has a viscosity of 50 cP or less when measured at 25° C.

Embodiment 72: A composition according to embodiment 71, which has a viscosity of between 1 and 10 cP or less when measured at 25° C.

Embodiment 73: A composition according to embodiment 71 or embodiment 72, which has a viscosity of between 2 and 10 cP or less when measured at 25° C.

Embodiment 74: A composition according to embodiment 1, which comprises:
  (a) ≥50 mg/ml of a protein, which is an antibody;
  (b) 30 mM or lower of a salt, such as sodium chloride or magnesium chloride;
  (c) 50 mM or lower of a buffer such as histidine buffer;
  (d) 0-25 mM of an amino acid, such as arginine or glycine;
  (e) 0.001-0.005% of a non-ionic surfactant;
  (f) 100-200 mM of a tonicity modifying agent, such as sucrose, propylene glycol, glycerol, mannitol or D-sorbitol;
buffered to a pH of between 5 and 7.

Embodiment 75: A composition according to embodiment 1, which comprises:
  (a) 100 mg/ml of a protein, which is an antibody;
  (b) 25 mM sodium chloride;
  (c) 33 mM histidine buffer;
  (d) 25 mM arginine;
  (e) 0.001% polysorbate 80;
  (f) 150 mM sucrose;
buffered to a pH of between 5 and 7.

Embodiment 76: A composition according to embodiment 1, which comprises:
  (a) 100 mg/ml of a protein, which is an antibody;
  (b) 25 mM sodium chloride;
  (c) 33 mM histidine buffer;
  (d) 25 mM arginine;
  (e) 0.001% polysorbate 80;
  (f) 150 mM mannitol;
buffered to a pH of between 5 and 7.

Embodiment 77: A composition according to embodiment 1, which comprises:
  (a) 100 mg/ml of a protein, which is an antibody;
  (b) 25 mM sodium chloride;
  (c) 33 mM histidine buffer;
  (d) 25 mM arginine;
  (e) 0.001% polysorbate 80;
  (f) 150 mM sucrose;
buffered to a pH of 6.5.

Embodiment 78: A composition according to embodiment 1, which comprises:
(a) 100 mg/ml of a protein, which is an antibody;
(b) 25 mM sodium chloride;
(c) 33 mM histidine buffer;
(d) 25 mM arginine;
(e) 150 mM sucrose;
Buffered to a pH between 5 and 7.

Embodiment 79: A composition according to any of the embodiments 1-78, wherein the composition is stable at room temperature.

Embodiment 80: A composition according to any of the embodiments 1-79, wherein the composition is stable at temperatures between 15 and 30° C.

Embodiment 81: A composition according to any of embodiments 1 to 80, wherein the protein is a monoclonal antibody.

Embodiment 82: A composition according to embodiment 65 or 81, wherein the antibody is of the IgG4 subtype.

Embodiment 83: A composition according to embodiment 65, 81 or 82, wherein the monoclonal antibody is an anti-IL20 monoclonal antibody.

Embodiment 84: A composition according to embodiment 65, 81 or 82, wherein the monoclonal antibody is an anti-TFPI monoclonal antibody.

Embodiment 85: A composition according to embodiment 65, 81 or 82, wherein the monoclonal antibody is an anti-C5aR monoclonal antibody.

Embodiment 86: A composition according to embodiment 65, 81 or 82, wherein the monoclonal antibody is an anti-NKG2D monoclonal antibody.

Embodiment 87: A composition according to embodiment 65, 81 or 82, wherein the monoclonal antibody is an anti-NKG2A monoclonal antibody.

Embodiment 88: A stable protein composition according to any of embodiments 1 to 87 for use in therapy.

Embodiment 89: A method of treating an inflammatory disease which comprises administering to a patient a therapeutically effective amount of a composition according to embodiment 83.

Embodiment 90: A composition according to embodiment 83 for use in the treatment of an inflammatory disease.

Embodiment 91: Use of a composition according to embodiment 83 in the manufacture of a medicament for the treatment of an inflammatory disease.

Embodiment 92: A pharmaceutical composition comprising an anti-IL20 composition according to embodiment 83 for use in the treatment of an inflammatory disease.

Embodiment 93: A method of treating a coagulopathy which comprises administering to a patient a therapeutically effective amount of a composition according to embodiment 84.

Embodiment 94: A composition according to embodiment 84 for use in the treatment of a coagulopathy.

Embodiment 95: Use of a composition according to embodiment 84 in the manufacture of a medicament for the treatment of a coagulopathy.

Embodiment 96: A pharmaceutical composition comprising an anti-TFPI composition according to embodiment 84 for use in the treatment of a coagulopathy.

Embodiment 97: A method of treating an inflammatory disease which comprises administering to a patient a therapeutically effective amount of a composition according to embodiment 84.

Embodiment 98: A composition according to embodiment 85 for use in the treatment of an inflammatory disease.

Embodiment 99: Use of a composition according to embodiment 85 in the manufacture of a medicament for the treatment of an inflammatory disease.

Embodiment 100: A pharmaceutical composition comprising an anti-C5aR composition according to embodiment 85 for use in the treatment of an inflammatory disease.

Embodiment 101: A method of treating an inflammatory disease which comprises administering to a patient a therapeutically effective amount of a composition according to embodiment 86.

Embodiment 102: A composition according to embodiment 86 for use in the treatment of an inflammatory disease.

Embodiment 103: Use of a composition according to embodiment 86 in the manufacture of a medicament for the treatment of an inflammatory disease.

Embodiment 104: A pharmaceutical composition comprising an anti-NKG2D composition according to embodiment 86 for use in the treatment of an inflammatory disease.

Embodiment 105: A method of treating an inflammatory disease which comprises administering to a patient a therapeutically effective amount of a composition according to embodiment 87.

Embodiment 106: A composition according to embodiment 87 for use in the treatment of an inflammatory disease.

Embodiment 107: Use of a composition according to embodiment 87 in the manufacture of a medicament for the treatment of an inflammatory disease.

Embodiment 108: A pharmaceutical composition comprising an anti-NKG2A composition according to embodiment 87 for use in the treatment of an inflammatory disease.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate). When a range is given, the range includes both end values, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The invention claimed is:

1. A stable, liquid composition comprising an anti-TFPI monoclonal antibody, a salt and/or a buffer, wherein the total concentration of said salt and/or buffer is lower than 100 mM and said anti-TFPI antibody is HzTFPI4F36.

2. The composition according to claim 1, wherein the total concentration of said salt and/or buffer is lower than 60 mM.

3. The composition according to claim 1, which does not comprise a surfactant.

4. The composition according to claim 1, wherein the anti-TFPI monoclonal antibody is present within the composition in a concentration of between 100 mg/ml and 300 mg/ml.

5. The composition according to claim 1, which has a viscosity of 50 cP or less when measured at 25° C.

6. A stable, liquid composition comprising an anti-TFPI monoclonal antibody and arginine, wherein the arginine is present in a concentration of between 5 mM and 100 mM and said anti-TFPI antibody is HzTFPI4F36.

7. The composition according to claim 6, wherein the concentration of arginine is between 5 mM and 30 mM.

8. The composition according to claim 1, wherein the anti-TFPI monoclonal antibody is of the IgG4 subtype.

9. A method of treating a coagulopathy which comprises administering to a patient a therapeutically effective amount of a composition according to claim 1.

10. The method of claim 9, wherein said coagulopathy is haemophilia A or haemophilia B.

11. The composition according to claim 1, wherein the anti-TFPI monoclonal antibody protein is present within the composition in a concentration of between 100 mg/ml and 150 mg/ml.

12. The composition according to claim 1, which has a viscosity of 10 cP or less when measured at 25° C.

13. The composition according to claim 1, wherein the composition shows a 4.5% or less increase in % HMWP after storage at 40° C. for up to 3 months.

14. The composition according to claim 6, wherein the composition shows a 4.5% or less increase in % HMWP after storage at 40° C. for up to 3 months.

15. The composition of claim 1, wherein said anti-TFPI monoclonal antibody is HzTFPI4F36 wherein the concentration of the antibody is at 100 mg/ml.

16. The composition of claim 6, wherein said anti-TFPI monoclonal antibody is HzTFPI4F36 wherein the concentration of the antibody is at 100 mg/ml.

* * * * *

UNITED STATES PATENT AND TRADEMARK OFFICE
CERTIFICATE OF CORRECTION

PATENT NO. : 9,795,674 B2
APPLICATION NO. : 13/580041
DATED : October 24, 2017
INVENTOR(S) : Parshad It is certified that error appears in the above-identified patent and that said Letters Patent is hereby corrected as shown below:

On the Title Page

Item (75) Inventors should read as follows:
-- Henrik Parshad, Viby Sj. (DK). --

Signed and Sealed this
Tenth Day of July, 2018

Andrei Iancu
*Director of the United States Patent and Trademark Office*